United States Patent [19]

Kelly et al.

[11] Patent Number: 5,166,208

[45] Date of Patent: Nov. 24, 1992

[54] FREDERICAMYCIN A DERIVATIVES

[75] Inventors: Thomas R. Kelly, Watertown, Mass.; Qun Li, Gurnee, Ill.; Vidya B. Lohray, Pune, India

[73] Assignee: Boston College, Chestnut Hill, Mass.

[21] Appl. No.: 774,780

[22] Filed: Oct. 9, 1991

[51] Int. Cl.$^5$ .................. C07D 221/20; A61K 31/435
[52] U.S. Cl. ...................................... 514/278; 546/15
[58] Field of Search ........................... 546/15; 514/278

[56] References Cited

U.S. PATENT DOCUMENTS 4,584,377  4/1986  Yokoi et al. ........................... 546/15
4,673,678  6/1987  Misra .................................... 514/278

FOREIGN PATENT DOCUMENTS 60-42368    3/1985  Japan .
60-56960    4/1985  Japan .
60-58964    4/1985  Japan .
60-152468   8/1985  Japan .

OTHER PUBLICATIONS

Bolger et al., *J. Org. Chem.*, 56, 2115 (1991).
Merck Index, p. 667 (11th. ed., 1989).
Kelly et al., *J. Am. Chem. Soc.*, 110, 6471 (1988).
R. C. Panday et al., *J. Antibiot.*, 34, 1389 (1981).
R. Misra et al., *J. Am. Chem. Soc.*, 104, 4478 (1982).
R. Misra et al., *J. Antibiot.*, 40, 786 (1987).
K. M. Byrne et al., *Biochemistry*, 24, 478 (1985).
D. J. Warnick-Pickle et al., *J. Antibiot*, 34, 1402 (1981).
R. Misra, *J. Antibiot.*, 51, 976 (1988).
N. S. Dalal et al., *Biochemistry*, 28, 748 (1989).
M. D. Latham et al., *Cancer Chemother. Pharmacol.*, 24, 167 (1989).
T. R. Kelly et al., *J. Am. Chem. Soc.*, 108, 7100 (1986).
A. V. R. Rao et al., *J. Chem. Soc., Chem. Commun.*, 1119 (1984).
K. A. Parker et al., *Tetrahedron Lett.*, 26, 2181 (1985).
A. S. Kende et al., *Tetrahedron Lett.*, 26, 3063 (1985).
G. Eck et al., *Tetrahedron Lett.*, 26, 4723 (1985).
G. Eck et al., *Tetrahedron Lett.*, 26, 4725 (1985).
M. Braun et al., *Tetrahedron Lett.*, 27, 179 (1986).
K. R. Acharya et al., *Acta Crystallogr., Sect. C. Cyst. Struct. Commun.*, 42, 334 (1986).
R. D. Bach et al., *J. Org. Chem.*, 51, 749 (1986).
S. M. Bennett et al., *J. Chem. Soc., Chem. Commun.*, 878 (1986).
R. D. Bach et al., *Tetrahedron Lett.*, 27, 1983 (1986).
K. A. Parker et al., *Tetrahedron Lett.*, 27, 3835 (1986).
A. V. R. Rao, In "Organic Synthesis Modern Trends, Proceedings of the 6th IUPAC Symposium", Chizhov, O. S. Ed.; Blackwell, Oxford, p. 75 (1987).
M. A. Ciufolini et al., *Tetrahedron Lett.*, 28, 171 (1987).
K. A. Parker et al., *J. Org. Chem.*, 52, 183 (1987).
U. R. Khire et al., *Indian J. Chem.*, Sect. B, 26, 195 (1987).
A. V. R. Rao et al., *Tetrahedron Lett.*, 28, 451 (1987).
A. V. R. Rao et al., *Tetrahedron Lett.*, 28, 455 (1987).
G. Mehta et al., *Tetrahedron Lett.*, 28, 479 (1987).
D. L. J. Clive et al., *J. Heterocycl. Chem.*, 24, 509 (1987).
Y. Tanoue et al., *Bull. Chem. Soc. Jpn.*, 60, 2927 (1987).
S. N. Naik et al., *Synth. Commun.*, 18, 633 (1988).
A. V. R. Rao et al., *Indian J. Chem., Sect. B.*, 27, 1065 (1988).
M. A. Ciufolini et al., *J. Org. Chem.*, 53, 4149 (1988).
J. C. Evans et al., *J. Org. Chem.*, 53, 5519 (1988).
M. Julia et al., *Heterocycles*, 28, 71 (1989).
A. V. R. Rao et al., *J. Chem. Soc., Chem. Commun*, 400 (1989).
M. Toyota et al., *Tetrahedron Lett.*, 30, 829 (1989).
D. L. Boger et al., *Tetrahedron Lett.*, 30, 2037 (1989).
I. S. Aidhen et al., *Tetrahedron Lett.*, 30, 5323 (1989).
B. Pandey et al., *J. Chem. Soc., Chem. Commun.*, 1791 (1990).
D. L. Boger et al., *J. Org. Chem.*, 55, 1919 (1990).
A. V. R. Rao et al., *Indian J. Chem., Sect. B*, 30B, 723 (1991).
L. Set et al., *J. Chem. Soc., Chem. Commun.*, 1205 (1985).
D. L. J. Clive et al., *J. Chem. Soc., Chem. Commun.*, 1755 (1991).
D. J. Clive et al., *J. Chem. Soc., Perkin Trans I*, 1433 (1991).
D. L. J. Clive et al., *J. Chem. Soc., Chem. Commun.*, 1520 (1987).
D. L. J. Clive et al., *Tetrahedron Lett.*, 32, 7159 (1981).

Primary Examiner—C. Warren Ivy
Assistant Examiner—Ba K. Trinh
Attorney, Agent, or Firm—Sewall P. Bronstein; Peter F. Corless; Gregory D. Williams

[57] ABSTRACT

The invention pertains to derivatives of fredericamycin A, their preparation and pharmaceutical uses as antitumor agents.

11 Claims, No Drawings

FREDERICAMYCIN A DERIVATIVES

BACKGROUND OF THE INVENTION

1. Field of the Invention

The present invention pertains to fredericamycin A derivatives and compositions and uses thereof.

2. Background Art (±)-Fredericamycin A is an antitumor antibiotic by *Streotomyces griseus* and represents a new structural class of antibiotics containing a spiro[4,4]nonane ring system. See *Merck Index*, p. 667 (11th ed., 1989). Isolation of the compound together with two biologically inactive components (fredericamycins B and C) was reported by R. Pandey, et al., *J. Antibiot.*, 34, 1389 (1981). The structure of the compound has been confirmed by x-ray crystallography as reported by R. Misra, *J. Am. Chem. Soc.*, 104, 4478 (1982). Spectroscopic and mass spectral characterization was reported in *J. Antibiot.*, 40, 786 (1987).

The biological activity and unique skeletal framework of fredericamycin A has prompted interest in the compound and its synthesis. See, for example, Boger, et al., *J. Org. Chem.*, 56, 2115 (1991); Kelly, et al., *J. Am Chem. Soc.*, 110, 6471 (1988); Kelly, et al., *J. Am. Chem. Soc.*, 108, 7100 (1986); Parker, et al., *Tetrahedron Letters.* 26, 2181 (1985); Byrne, et al., *Biochemistry*, 24, 478 (1985); and Rao, et al., *Chem. Commun.*, 1119 (1984). A study of the mechanism of action of fredericamycin A was reported by Hilton, et al., *Biochemistry*, 25, 5533 (1986). In vitro studies indicate fredericamycin A has cytotoxicity against p388 and L1210 mouse leukemias comparable to doxorubicin and actinomycin. See, Warnick-Pickle, et al., *J. Antibiot.*, 34, 1402 (1981); Chem. Abstr., 1985, 103, 104798c.

Preparation and biological activity of some water soluble salts of fredericamycin A have been reported. See, U.S. Pat. No. 4,673,678 and Misra, *J. Antibiot.*, 51, 976 (1988). Other compounds have been reported in U.S. Pat. No. 4,584,377.

SUMMARY OF THE INVENTION

The present invention provides compounds of the following Formula (I)

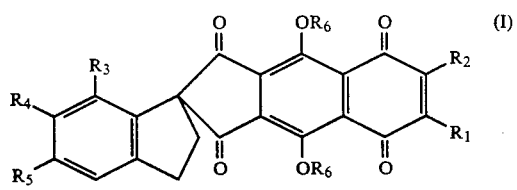

wherein:

$R_1$ and $R_2$ are each independently selected from the group consisting of hydrogen, halo, hydroxy, arylthio, lower alkylthio, substituted lower alkylthio, and a group selected from the following Formulas (IA) and (IB):

—N(R$_7$)R$_8$        (IA)

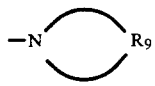

(IB)

wherein $R_7$ and $R_8$ are each independently selected from the group consisting of hydrogen, hydroxy, lower alkyl, substituted lower alkyl, alkenyl having 2 to 6 carbon atoms, alkynyl having 2 to 6 carbon atoms, lower alkoxy, lower alkoxycarbonyl, alkanoyl, cycloalkyl having 3 to 7 ring members, aryl, aryl substituted by lower alkyl, arylcarbonyl, amidino (—C(=NH)NH$_2$), dialkylaminocarbonyl having 3 to 12 carbon atoms, a heterocyclic group selected from the group consisting of heteroaromatic and heteroalicyclic groups having 1 to 2 rings, 3 to 7 ring members in each ring, and 1 to 3 hetero atoms, or a group of the following Formula (IC):

—NHR$_{10}$—S—S—R$_{11}$        (IC)

wherein $R_{10}$ is selected from the group consisting of alkylene having 1 to 6 carbon atoms, alkenylene having 2 to 6 carbon atoms, and aryl, any of which groups may be substituted at one or more available positions by one or more lower alkyl; and $R_{11}$ is selected from the group consisting of lower alkyl, substituted lower alkyl, cycloalkyl having 3 to 7 ring members, aryl, aryl substituted by lower alkyl, a heterocyclic group selected from the group consisting of heteroaromatic and heteroalicyclic groups having 1 to 2 rings, 3 to 7 ring members in each ring, and 1 to 3 hetero atoms, and said heterocyclic group substituted by one or more lower alkyl;

$R_9$ is selected from the group consisting of alkylene having 2 to 6 carbon atoms, heteroalkylene having 2 to 6 carbon atoms and 1 to 2 hetero atoms, alkenylene having 2 to 6 carbon atoms, alkynylene having 2 to 6 carbon atoms, any of which groups may be substituted at one or more available positions by one or more hydroxy, amino, halo, lower alkyl, substituted lower alkyl, lower alkylamino, substituted lower alkylamino, alkenyl having 2 to 6 carbon atoms, alkynyl having 2 to 6 carbon atoms, lower alkoxy, lower alkoxycarbonyl, lower alkoxycarbonylamino, dialkylaminocarbonylamino having 3 to 12 carbon atoms, guanidino, ureido (—NHCONH$_2$), and a group of the following Formula (ID):

—S—S—R$_{12}$        (ID)

wherein $R_{12}$ is selected from the group consisting of lower alkyl, substituted lower alkyl, cycloalkyl having 3 to 7 ring members, alkanoylamino, aryl, aryl substituted by lower alkyl, a heterocyclic group selected from the group consisting of heteroaromatic and heteroalicyclic groups having 1 to 2 rings, 3 to 7 ring members in each ring, and 1 to 3 hetero atoms, and said heterocyclic group substituted by one or more lower alkyl;

$R_3$ is selected from the group consisting of hydrogen, hydroxy, lower alkyl, and lower alkoxy;

$R_4$ and $R_5$ together form a ring selected from the following Formulas (IE) and (IF):

(IE)

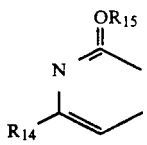 (IF)

wherein $R_{13}$ is selected from the group consisting of hydrogen, and lower alkyl; $R_{14}$ is selected from the group consisting of lower alkyl, alkenyl having 2 to 10 carbon atoms, and alkanoyl; $R_{15}$ is selected from the group consisting of hydrogen, lower alkyl, and alkanoyl;

$R_6$ is selected from the group consisting of hydrogen, alkanoyl, aryl carbonyl, and a pharmaceutically acceptable cation; and physiologically functional equivalents thereof including pharmaceutically acceptable salts thereof.

In another aspect, the present invention provides fredericamycin derivatives of the following Formula (II):

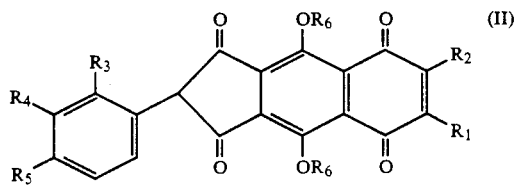 (II)

wherein:

$R_1$ and $R_2$ are each independently selected from the group consisting of hydrogen, halo, lower alkoxy, arylthio, lower alkylthio, substituted lower alkylthio, and a group selected from the following Formulas (IA) and (IB):

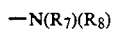 (IA)

 (IB)

wherein $R_7$ and $R_8$ are each independently selected from the group consisting of hydrogen, hydroxy, lower alkyl, substituted lower alkyl, alkenyl having 2 to 6 carbon atoms, alkynyl having 2 to 6 carbon atoms, lower alkoxy, lower alkoxycarbonyl, alkanoyl, cycloalkyl having 3 to 7 ring members, aryl, aryl substituted by lower alkyl, arylcarbonyl, amidino (—C(=NH)NH$_2$), dialkylaminocarbonyl having 3 to 12 carbon atoms, a heterocyclic group selected from the group consisting of heteroaromatic and heteroalicyclic groups having 1 to 2 rings, 3 to 7 ring members in each ring, and 1 to 3 hetero atoms, or a group of the following Formula (IC):

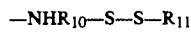 (IC)

wherein $R_{10}$ is selected from the group consisting of alkylene having 1 to 6 carbon atoms, alkenylene having 2 to 6 carbon atoms, and aryl, any of which groups may be substituted at one or more available positions by one or more lower alkyl; and $R_{11}$ is selected from the group consisting of lower alkyl, substituted lower alkyl, cycloalkyl having 3 to 7 ring members, aryl, aryl substituted by lower alkyl, a heterocyclic group selected from the group consisting of heteroaromatic and heteroalicyclic groups having 1 to 2 rings, 3 to 7 ring members in each ring, and 1 to 3 heteroatoms, and said heterocyclic group substituted by one or more lower alkyl;

$R_9$ is selected from the group consisting of alkylene having 2 to 6 carbon atoms, heteroalkylene having 2 to 6 carbon atoms and 1 to 2 hetero atoms, alkenylene having 2 to 6 carbon atoms, alkynylene having 2 to 6 carbon atoms, any of which groups may be substituted at one or more available positions by one or more hydroxy, amino, halo, lower alkyl, substituted lower alkyl, lower alkylamino, substituted lower alkylamino, alkenyl having 2 to 6 carbon atoms, alkynyl having 2 to 6 carbon atoms lower alkoxy, lower alkoxycarbonyl, lower alkoxycarbonylamino, dialkylaminocarbonylamino having 3 to 12 carbon atoms, guanidino, ureido (—NHCONH$_2$), and a group of the following Formula (ID):

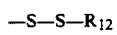 (ID)

wherein $R_{12}$ is selected from the group consisting of lower alkyl, substituted lower alkyl, cycloalkyl having 3 to 7 ring members, alkanoylamino, aryl, aryl substituted by lower alkyl, a heterocyclic group selected from the group consisting of heteroaromatic and heteroalicyclic groups having 1 to 2 rings, 3 to 7 members in each ring, and 1 to 3 hetero atoms, and said heterocyclic group substituted by one or more lower alkyl;

$R_3$ is selected from the group consisting of hydrogen, hydroxy, lower alkyl, and lower alkoxy;

$R_4$ is selected from the group consisting of hydrogen, hydroxy, lower alkylaminocarbonyl, and lower alkoxy;

$R_5$ is selected from the group consisting of hydrogen, hydroxy, lower alkyl, alkenyl having from 2 to 6 carbon atoms, and lower alkoxy; and $R_6$ is selected from the group consisting of hydrogen, alkanoyl, aryl carbonyl, and a pharmaceutically acceptable cation; and physiologically functional equivalents thereof, including pharmaceutically acceptable salts thereof.

The invention also includes compounds of a structure as defined for Formula (II) above, with the proviso that $R_1$ is not alkoxy, and/or $R_2$ is not alkoxy, and/or $R_3$ is other than hydroxy.

Preferred compounds of the invention include those of the above formulas where at least one of substituents $R_1$ and $R_2$ are hydrogen.

Phenyl and napthyl are preferred aryl groups of the compounds of the invention. A substituted aryl group can be substituted at one or more available positions by a variety of suitable substituents such as halogen, hydroxy, lower alkoxy, lower alkyl, amino, lower alkylamino, amino(lower alkyl), and lower alkoxycarbonyl.

The invention also provides a pharmaceutical composition comprising a suitable pharmaceutical carrier and one or more compounds of the invention, including compounds of Formulas (I) or (II), and a method of using a compound of the invention, including compounds of Formulas (I) or (II), to treat tumors in mammals. Further provided is a process for preparing compounds of the invention, the process being described in detail hereinafter.

As employed in herein, the term "lower alkyl" is intended to include those alkyl groups, of either a straight or branched chain configuration, which contain 1 to 8 carbons. The term "cycloalkyl" refers to unsubstituted cycloalkyl groups having from 3 to 7 carbon atoms as well as cycloalkyl groups having from 3 to 7 carbon atom ring members which are substituted at one or more available positions. Suitable substituents include, for example, substituents that are suitable for a substituted lower alkyl group.

The term "lower alkoxy" is intended to include those alkoxy groups (including alkoxy groups having more than one oxygen linkage) of either a straight or branched chain, which contain 1 to 8 carbon atoms.

The term "alkanoyl" is intended to include groups of the Formula —C(=O)R, wherein R is hydrogen or lower alkyl group.

The term "lower alkylthio" is intended to include those alkylthio groups (including alkylthio groups having more than one thio linkage) of either a straight or branched chain configuration, which contain 1 to 8 carbon atoms.

The term "substituted lower alkyl" is intended to include lower alkyl groups which were independently substituted at available positions by one or more suitable substituents such as hydroxy, halo, nitro, cyano, lower alkoxy, amino, lower alkylamino, lower alkoxycarbonylamino, guanidino, ureido, lower alkylureylene (—NHCONH-lower alkyl), alkanoylamino including alpha-amino acids and polypeptides of from 2 to 5 amino acids, lower alkoxycarboxyl, alkenyl having 2 to 6 carbons atoms, alkynyl having 2 to 6 carbon atoms, cycloalkyl having 3 to 7 ring members, cycloalkenyl having 5 to 7 ring members, a group of Formula —S—S—$R_{12}$ (ID) as defined above, and a heterocyclic group selected from the group consisting of heteroaromatic and heteroalicyclic groups having 1 to 2 rings, 3 to 7 ring members in each ring, and 1 to 3 hetero atoms.

The term "substituted lower alkylthio" is intended to include a substituted lower alkyl group which is bonded to a sulfur atom in a thio ether linkage.

DETAILED DESCRIPTION OF THE INVENTION

Compounds of Formulas (I) and (II) are prepared by the convergent synthesis of the general synthons 1 and 2 depicted in Scheme I below. Substituent X of 1 may be, for example, hydrogen or lower alkoxy. Throughout the following Schemes and discussion, substituents $R_1$ through $R_{15}$ are intended to mean the same as defined above.

Scheme I:

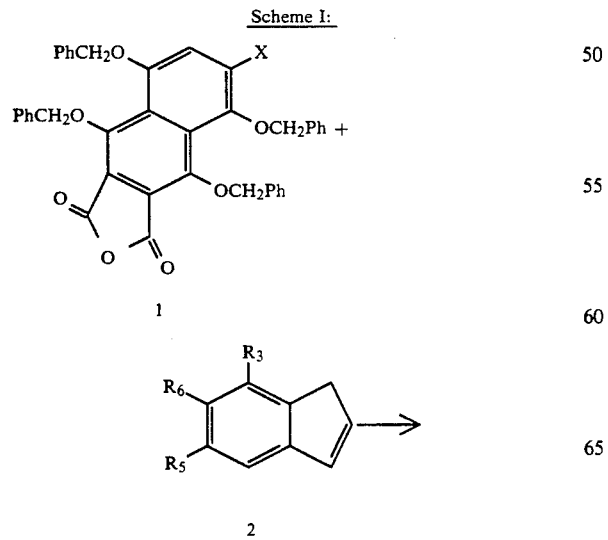

-continued
Scheme I:

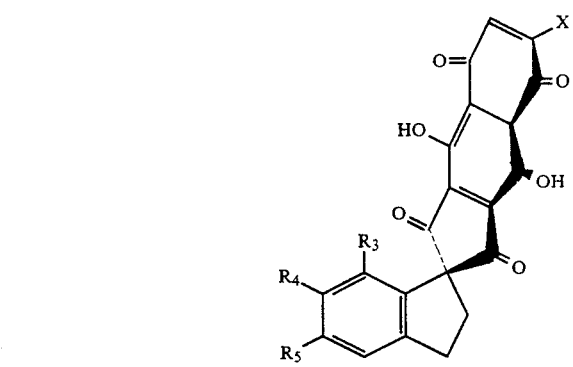

The anhydride synthon 1 can be prepared as in Scheme II:

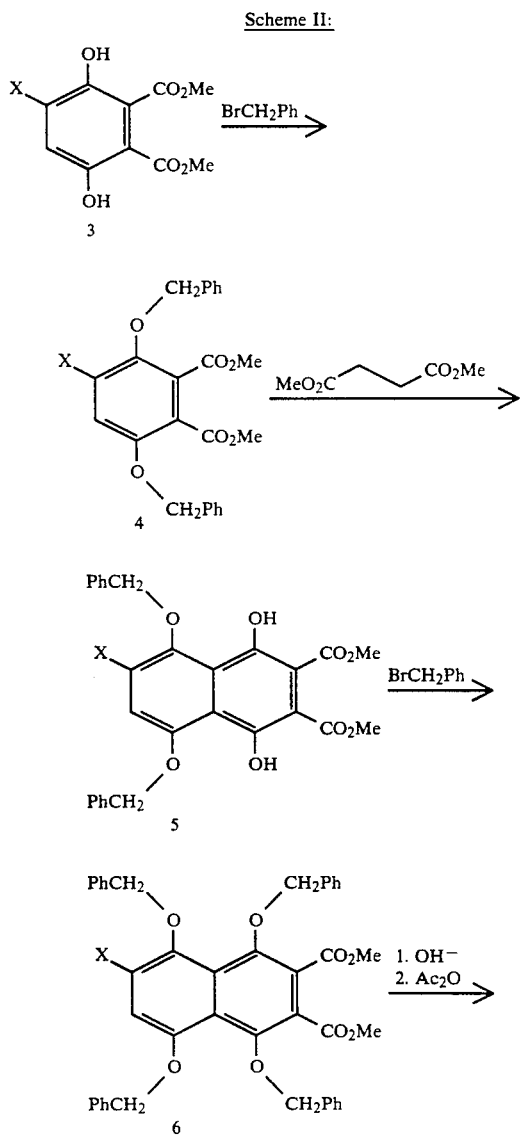

Scheme II:

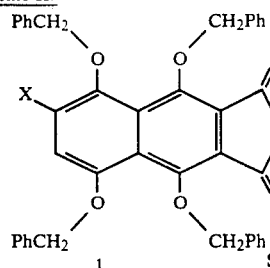

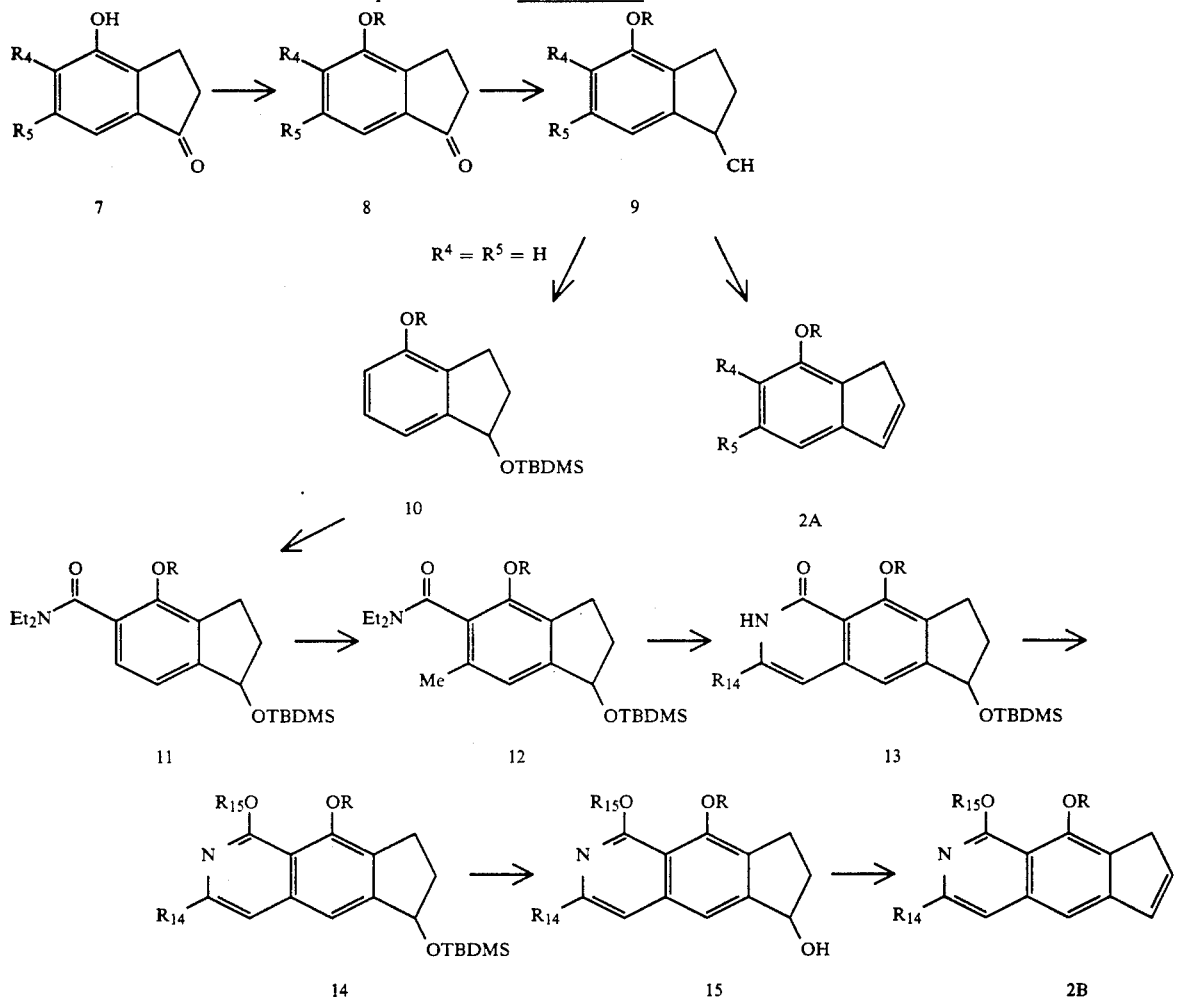

or 1,3-dimethyl-3,4,5,6-tetrahydro-2(1H)-pyrimidinone (DMPU).

Compound 5 is converted to 6 using the same benzylation reaction described above for the synthesis of 4. Compound 6 is hydrolyzed in the presence of base such as a sodium, potassium or lithium hydroxide at about 100° C. to give the phthalic diacid. Solvents such as a tetrahydrofuran/methanol mixture can be employed. The resultant crude diacid is condensed with acetic anhydride at reflux to yield the anhydride 1.

Hydroquinone phthalate 3 where X is hydrogen or lower alkoxy is prepared by methods disclosed in Kelly, et al., *J. Am. Chem. Soc.,* 110, 6471 (1988). The phthalate 3 is reacted with benzyl bromide or benzyl chloride at room temperature overnight in the presence of a suitable base such as potassium carbonate in acetone, dimethylformamide or other inert solvent to yield the dibenzyl phthalate 4. This compound 4 is then converted to the naphthoquinol 5 by condensation with dimethyl succinate in the presence of a base. Solvents such as tetrahydrofuran or ethyl ether are employed. Suitable bases include sodium bis(trimethylsilyl)amide In accordance with Scheme III, compound 7 is synthesized by the methods disclosed in Grieco, et al., *J. Org. Chem.,* 41, 1485 (1976). The indanone 7 is protected with a group R to afford 8, where group R is lower alkyl or lower alkoxy. Typically 7 is condensed with halo compound of Formula R-I or R-Cl in the presence of a base and in a solvent such as tetrahydrofuran, dimethylformamide or acetone. Suitable bases include N,N-diisopropylethylamine and potassium carbonate. The methyl ether (R above being $CH_{OCH_2}$—) is a preferred protecting group. Compound 8 is reduced at room temperature to provide the alcohol 9, for example by treatment with lithium aluminum hydride in solvent of tetrahydrofuran or ether, or treatment with sodium borohydride in an alcoholic solvent such as methanol or ethanol. The alcohol 9 is dehydrated to the indene derivative 2A by reaction with o-nitrophenyl selenocyanate and tri-n-butylphosphine in tetrahydrofuran followed by oxidation of the selenide with hydrogen peroxide (30 wt. % in $H_2O$) at 0° C.

To synthesize the isoquinoline 2B, the silyl ether 10 is prepared by reaction of 9 where both $R_4$ and $R_5$ are hydrogen, with t-butyldimethylsilylchloride at room temperature in the presence of imidazole in dimethylformamide or other suitable solvent. Other bases also may be employed.

Annelation of the ring is achieved by three successive metalation reactions. More specifically, 10 is treated with butyllithium, preferably sec-butyllithium, at −78° C. in an anhydrous solvent such as tetrahydrofuran followed by reaction with diethylcarbamoyl chloride and overnight stirring at room temperature to provide the amide 11. The ring is methylated to yield 12 by treatment of 11 with butyllithium, preferably t-butyllithium, at −78° C. in tetrahydrofuran, and quenching the resulting anions with methyl iodide. Isoquinolines of the structure 13 are obtained by lithiation of 12 with butyllithium, e.g. n-butyllithium, preferably in the presence of 2,2,6,6,-tetramethylpiperidine in tetrahydrofuran at −78° C., and quenching the anions with a nitrile of the Formula $R_{14}CN$, wherein the group $R_{14}$ is the same as described above for Formulas (IE) and (IF). Suitable nitriles of the structure $R_{14}CN$ include, for example, diethoxyacetonitrile (Chemical Dynamics Corporation), hexanenitrile and benzonitrile. Use of diethoxyacetonitrile provides $R_{14}$ as the diethoxy benzylic group which can be later hydroylzed to the aldehyde.

Compounds of structure 14 are provided by reaction of 13 with a lower alkyl-iodide of the Formula $R_{15}I$ in the presence of silver oxide or other silver salt and benzene, acetone or other suitable solvent with sonication in the dark under an argon atmosphere for 5 or 6 days. The silyl group is cleaved to afford 15 by addition of fluoride (n-$Bu_4NF$) to 14 at 0° C. to room temperature. Dehydration of 15 to provide compound 2B is achieved using o-nitrophenyl selenocyanate and tri-n-butylphosphine in tetrahydrofuran followed by oxidation of the resulting selenide with hydrogen peroxide (30 wt. % in $H_2O$) at 0° C.

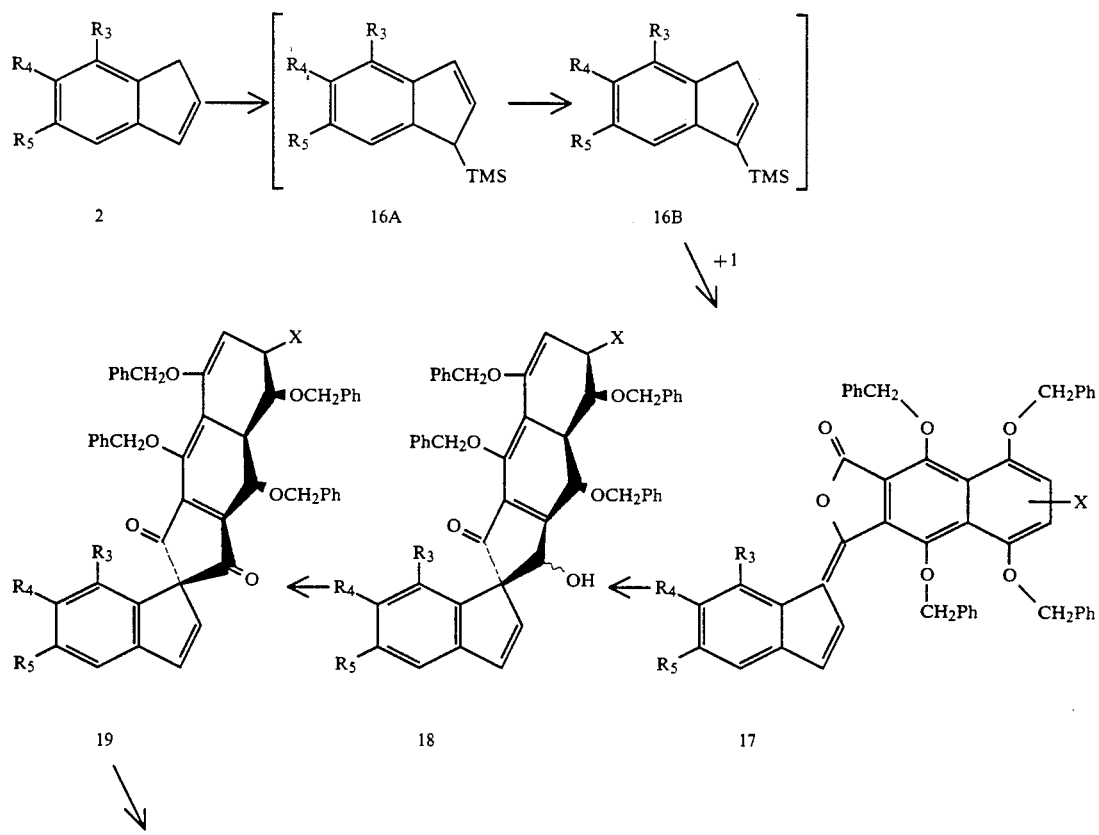

Scheme IV:

-continued
Scheme IV:

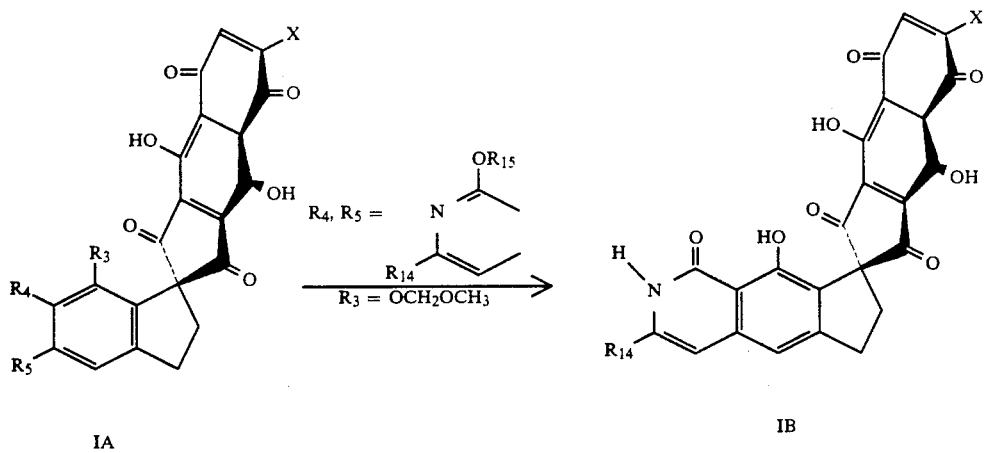

IA

IB

The general coupling reaction of the convergent synthesis is depicted in Scheme IV. The pentene 2 may be of the Formula of either 2A or 2B as shown in Scheme III and described above. The compound is silylated to afford 16A by treatment with one equivalent of butyllithium, e.g. n-butyllithium or t-butyllithium, in anhydrous tetrahydrofuran at −78° C., followed by quenching of the resulting anions with one equivalent of trimethylsilyl chloride. Without isolation of 16A, the silyl anion 16B is generated by addition of another equivalent of butyllithium at −78° C. The anhydride 1 dissolved in tetrahydrofuran or other suitable solvent is added to the anion 16B at −78° C., followed by the addition of an equivalent of sodium bis(trimethylsilyl)amide. Subsequent addition of acetic anhydride in tetrahydrofuran at room temperature provides the lactone 17. The spiroketo-alcohol 18 is synthesized as a diastereometric mixture by reduction of 17 with diisobutylaluminum hydride at −78° C. in a suitable solvent such as methylene chloride or toluene, and cyclizing the keto-aldo compound by treatment with potassium carbonate or other suitable base. Compound 19 is provided by oxidation of 18, preferably by Swern-type oxidation (i.e., addition of oxalyl chloride/dimethylsulfoxide followed by triethylamine), or treatment with pyridinium dichromate in a solvent such as methylene chloride.

Hydrogenation of 19 over palladium on activated carbon saturates the indene double bond as well as cleaves the four benzyl ethers. Compound IA can be provided by in situ oxidation of the hydrogenation product of 19 by opening the hydrogenation reaction vessel to the air and stirring at room temperature. Compound IA is further deprotected by refluxing the compound in the presence of sodium bromide and p-toluenesulfonic acid in methanol to provide IB. Compound 19 can also be heated (ca. 100° C.) in a sealed tube with a suitable alkylating agent, e.g. methyl iodide, to provide compounds where substituent $R_{13}$ is lower alkyl.

Scheme V:

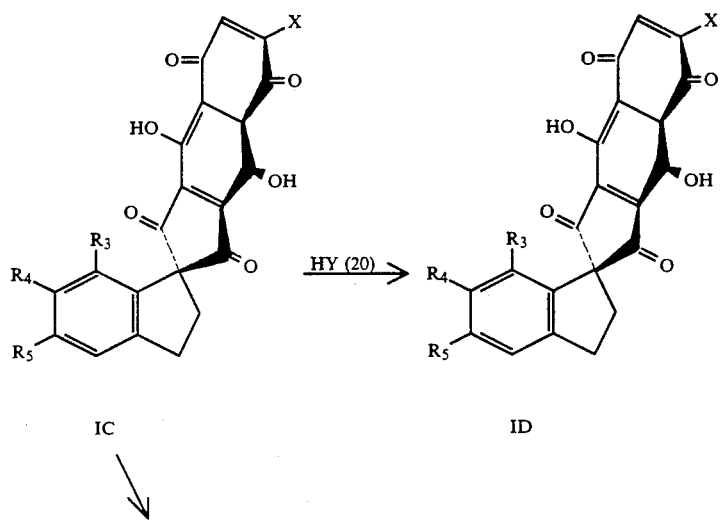

IC

ID

Scheme V:

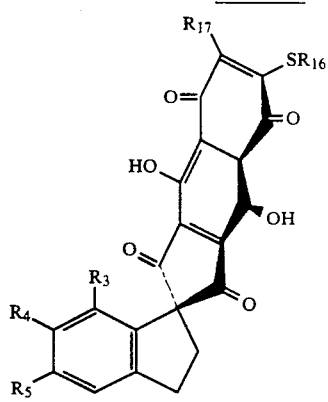

IE

Compounds of structure IC, wherein substituent X is hydrogen or lower alkoxy, undergo nucleophilic addition as depicted in Scheme V. Compounds of structure ID may be prepared by stirring compound IC at 0° C. to room temperature (ca. 20° C.) with at least one molar equivalent of an amine HY and solvent for a time sufficient to result in the formation of the amine substituted derivative. This addition reaction typically proceeds to completion within one to two hours. Suitable solvents include tetrahydrofuran, methylene chloride or alcoholic solvents such as methanol or ethanol, or a mixture of solvents such as a methanol and tetrahydrofuran mixture. After addition is complete, the solvent is removed under reduced pressure and the desired product can be purified by conventional means including column chromatography.

The amine group Y as shown above in compounds 20 and ID is suitably a variety of moieties, including the groups of the structure:

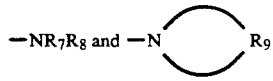

Other suitable amines that will undergo nucleophilic addition to IC include hydroxyl amine and alkylated derivatives thereof such as ethylhydroxylamine.

Aminodisulfides of the structure —NHR$_{10}$—S—S—R$_{11}$ (Formula IC above) also undergo addition to IC. These compounds may be prepared by various methods including reaction of thiol of structure R$_{11}$SH with a Bunte salt of the structure NH$_2$R$_{10}$SO$_3$Na by procedures described by Klayman, et al., *J. Org. Chem.*, 29, 3737 (1984). Aminodisulfides also are suitably prepared by reaction of thiol R$_{11}$SH with a sulfenylthiocarbonate of structure NH$_2$R$_{10}$SSC(=O)OMe$_3$ as described by Brois, et al., *J. Am. Chem. Soc.*, 92, 7269 (1970); or by reaction of thiol R$_{11}$SH with a 3-nitro-2-pyridyldisulfide of the structure

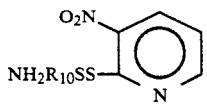

by a disulfide thiol exchange reaction as disclosed in Matseuda, et al., *Chem. Lett.*, 951 (1978). Alternatively, the above shown 3-nitro-2-pyridyldisulfide may be directly added to the napthoquinone moiety of IC, and then the addition product treated with thiol of structure R$_{11}$SH in the presence of a tertiary amine or other suitable base and an inert solvent such as methanol to afford the compound ID.

Thiols may also undergo nucleophilic addition to the napthoquinone moiety of IC to afford compounds IE. Suitable thiol addition reagents include compounds of structure R$_{16}$SH, wherein the group R$_{16}$ is, for example, lower alkyl, aryl, cycolalkyl having 3 to 7 carbon atoms, and a heterocyclic group selected from the group consisting of heteroaromatic or heteroalicyclic groups having from 1 to 2 rings, 3 to 7 members in each ring, and from 1 to 3 hetero atoms. By varying the amount of thiol employed and reaction temperature, the napthoquinone may be mono-substituted (i.e., R$_{17}$ of compound IE is hydrogen) or disubstituted (i.e., R$_{17}$ of compound IE is the same as SR$_{16}$) The reaction is typically carried out by stirring at least molar equivalent of the thiol and the compound IC at −20° C. to room temperature for a time sufficient to result in formation of the thio-substituted derivative. Typically the thiol additions require longer reaction times than the amine additions, and proceed to completion at room temperature with stirring in about 15 to 20 hours. Solvents such as methanol, tetrahydrofuran or methylene chloride, or mixtures thereof, may be used. After reaction completion, the solvent is removed under reduced pressure, and the reaction product purified by column chromatography or other conventional means.

Halides will add to the napthoquinone moiety of IC to afford compounds where substituents R$_1$ or R$_2$ are halo. Suitable reactions conditions include stirring compound IC in a suitable solvent such as methanol with, for example, iodine or bromine for a time and temperature sufficient to complete the addition reaction.

A variety of compounds of Formula (I) can be prepared where substituent $R_{14}$ is an acetal group. For example, acetal $R_{14}$ can be hydrolyzed to an alkanoyl moiety by stirring the compound with dilute (e.g., 0.015M) aqueous hydrochloric acid solution at room temperature.

A variety of compounds of Formula (I) also can be prepared where substituent $R_{14}$ is alkanoyl. For instance, a variety of Wittig-type reagents may be condensed with an aldehyde moiety to provide an alkene which, in turn, may be further modified to provide other groups. Suitable Wittig-type reagents include trans-2-butenyltriphenylphosphonium bromide, prepared by the procedures described in Bohlmann, et al., Chem. Ber., 89, 1307–1315 (1956); and Hug, et al., Helv. Chim. Acta., 55, 1828–1845 (1972). The condensation reaction is typically carried out by adding a base to the Wittig reagent at 0° C., and adding the thus formed ylide to the aldehyde derivative in a tetrahydrofuran solution cooled to −78° C. After stirring for several minutes after the addition, the reaction may be quenched with methanol. The reaction provides a mixture of geometric isomers, which can be isomerized to the thermodynamically more stable trans,trans-pentadienyl isomer by refluxing the compound in methanol in the presence of iodine. Such an alkene may be hydrogenated with a palladium catalyst to the corresponding alkane. An alkanoyl group $R_{14}$ may be functionalized in a variety of other ways by procedures known to those skilled in the art, for example reduced to an alcohol or oxidized to the corresponding acid or ester.

As discussed above, the isoquinoline methyl (i.e., the substituent $R_{15}$ of Formula (I) being methyl) and/or methyl methyl ether (MOM) ethers can be removed by refluxing the compound in a suitable solvent such as methanol with p-toluenesulfonic acid and anhydrous sodium bromide for up to 1.5 hours. When the $R_{14}$ substituent is 1,3-pentadienyl, both the diene can be isomerized to the trans,trans isomer and the $R_{15}$ protecting group ether removed by a one-pot procedure by refluxing the diene with anhydrous sodium bromide, p-toluenesulfonic acid and a crystal of iodine in methanol for about 15 minutes.

Other compounds of Formula (I) can be prepared in accordance with Scheme VI.

Scheme VI:

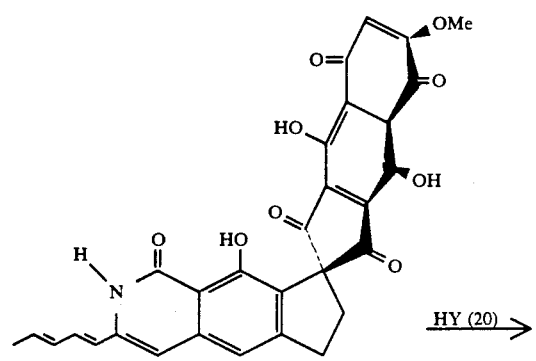

21

-continued
Scheme VI:

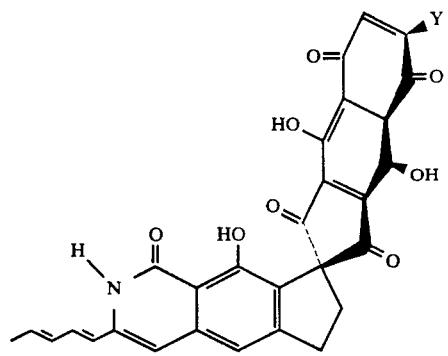

1F

As shown in Scheme VI, fredericamycin A, compound 21, can react with amines of structure HY (20) where the methoxy group of the napthoquinone moiety of 21 is replaced by the amine group Y. The amine 20 shown in Scheme VI, can be the same as discussed above in reference to Scheme V. Compounds of structure IF may be prepared by dissolving 21 in a suitable inert solvent and then adding a molar excess of the amine HY at 0° C. to room temperature. Suitable inert solvents include tetrahydrofuran, or a solvent mixture such as a mixture of tetrahydrofuran and methanol or a mixture of methylene chloride and methanol. The reaction mixture is stirred for a time sufficient to complete the addition reaction. The solvent then can be removed under reduced pressure and the reaction product IF purified by conventional means including column chromatography.

Physiologically functional equivalents of the compounds of Formulas (I) and (II) include pharmaceutically acceptable salts, esters and amides modifications of the compounds which do not diminish the compound's activity to an unacceptable level. Pharmaceutically acceptable salts of compounds of Formulas (I) and (II) can be prepared in a number of ways known in the art. For example, where the compound comprises an amino group, pharmaceutically suitable salts include those resulting from treatment with acetic, hydrochloric, citric, sulfuric, phosphoric, succinic, fumaria, ascorbic, and glutaric acid. Where the compound comprises a carboxy group, pharmaceutically suitable salts include alkali metal salts of the acid, for example a sodium salt. Examples of pharmaceutically acceptable esters of compounds of Formulas (I) and (II) include arylcarbonyl ester and alkanoyl ester derivatives and are prepared by conventional methods. Examples of pharmaceutically acceptable amides of compounds of Formulas (I) and (II) include treatment of compounds where substituents $R_1$ and/or $R_2$ are amino or alkylamino, with alkylcarboxylic acids having 1 to 12 carbon atoms, for example, propionic acid, and arylcarboxylic acids, for example 4-chlorobenzoic acid.

Pharmaceutically acceptable cations that suitably serve as substituent $R_6$ of the compounds of Formulas (I) and (II) include alkali metals (lithium, sodium and potassium), magnesium, calcium, ferrous, ferric, ammonium, alkylammonium including tetraalkylammonium, guanidinium, and protected forms of lysine, procaine and choline. Where compounds of Formulas (I) and (II)

are prepared in the phenol form (i.e., substituent $R_6$ is hydrogen), addition of a base form of the cation will yield the corresponding cationic compound of Formulas (I) and (II).

The antitumor activity of the compounds of Formulas (I) and (II) has been demonstrated in recognized in vitro and in vivo screens, including activity against p388 murine leukemia.

The activity against tumors is evidenced by reduction of tumor cells in mammals (e.g., mice bearing tumors) and consequent increase in survival duration as compared to an untreated tumor bearing control group.

Antitumor activity in the tumor tests disclosed herein has been reported to be indicative of antitumor activity in man. See, for example, A. Goldin, et al., in *Methods in Cancer Research*, ed. V. T. DeVita Jr. and H. Busch, 16, 165, Academic Press, N.Y. 1979.

Accordingly, the compounds of the present invention are useful as pharmaceuticals for the treatment of mammals, including humans, particularly for the treatment of mammals having tumors susceptible to the compounds of the invention. Thus, the invention provides a method for the treatment of tumors in mammals, including humans, the method comprising administration of an antitumor effective amount of one or more compounds of Formulas (I) or (II) in a pharmaceutically useful form, once or several times a day or other appropriate schedule, orally, rectally, parenterally, or applied topically.

For such treatment, the compounds of the invention are administered in effective amounts and in appropriate dosage form ultimately at the discretion of the medical or veterinary practitioner. For example, as known to those skilled in the art, the amount of compound of Formulas (I) or (II) required to be pharmaceutically effective will vary with a number of factors such as the mammal's weight, age and general health, the efficacy of the particular compound and formulation, route of administration, nature and extent of the condition being treated, and the effect desired. The total daily dose may be given as a single dose, multiple doses, or intravenously for a selected period. Any suitable route of administration may be employed, for example, oral, parenteral, intramuscular and the like. Appropriate dosage forms include troches, dispersions, suspensions, solutions, capsules, and the like for oral administration; and suspensions, solutions, emulsions in an aqueous or non-aqueous liquid such as a syrup, and the like for parenteral administration.

In another embodiment, the present invention provides pharmaceutical compositions containing one or more compounds of Formulas (I) or (II) together with a pharmaceutically acceptable carrier. Methods of preparation of such compositions are well known in the art and in general include the process of uniformly mixing the active compound with the carrier. Suitable carriers include pharmaceutically acceptable liquids and finely dispersed solids, and, if required, shaping the product into the desired formulation. In general, water, a suitable oil, isotonic saline, aqueous dextrose (glucose), and related sugar solutions and glycols such as propylene glycol or polyethylene glycols are suitable carriers for parenteral solutions. Suitable pharmaceutical carriers are also described in Remington's Pharmaceutical Sciences.

A parenteral composition suitable for administration by injection can be made by adding an effective amount of the active compound in ten percent by volume propylene glycol and water. The solution is made isotonic with sodium chloride and sterilized.

A tablet of one or more compounds of the invention may be made by compression or molding, optionally with one or more accessory ingredients. Compressed tablets may be prepared by compressing in a suitable machine, the active compound in a free-flowing form such as a powder or granules, optionally mixed with a binder, lubricant, inert diluent, surfactant, or dispersing agent. Molded tablets may be made by molding in a suitable machine, a mixture of the powdered active compound with any suitable carrier.

A syrup may be made by adding the active compound to a concentrated, aqueous solution of a sugar for example sucrose to which may also be added any accessory ingredient. Such accessory ingredient(s) may include flavorings, an agent to retard crystallization of the sugar or an agent to increase the solubility of any other ingredient, such as a polyhydric alcohol (e.g. glycerol or sorbitol).

Formulations for rectal administration may be presented as a suppository with a usual carrier such as cocoa butter. Formulations suitable for parenteral administration conveniently comprise a sterile aqueous preparation of the active compound which is preferably isotonic with the blood of the recipient.

In addition to the aforementioned ingredients, the formulations of this invention may further include one or more accessory ingredient(s) selected from dilutents, buffers, flavoring agents, binders, surface active agents, thickeners, lubricants, preservatives (including antioxidants) and the like.

All cited references are incorporated herein by reference.

The following Examples are provided by the way of illustration of the present invention and should in no way be construed as limiting.

GENERAL COMMENTS

In the following Examples, all solvents were reagent grade and used without further purification with the following exceptions. Immediately before use, tetrahydrofuran (THF) was dried by distillation from sodium benzophenone ketyl, and methylene chloride was dried by distillation over calcium hydride. Water or air sensitive reactions were conducted in oven or flame dried glassware under an atmosphere of dry argon. Flash column chromatography was performed using $SiO_2$ (EM Science Silica gel 60, average particle size 60 nm) packed as a slurry of the eluting solvent. A layer of washed sand was optionally added to the top of the $SiO_2$ and then the material to be purified added and eluted under a positive pressure of nitrogen or argon.

$^1H$ NMR data was recorded on a Varian XL-300 spectrometer with chemical shifts reported in parts per million (ppm) downfield from tetramethylsilane.

Products were vacuum oven dried. Temperatures are in degrees centigrade. All compounds are racemic mixtures of enantiomers or diastereoisomers unless otherwise specified.

EXAMPLE 1

Preparation of
6'7'-Dihydro-6-ethylamino-2',6',7'-trihydro-4,9,9'-trihydroxy-3'-(1,3-pentadienyl)spiro[2H-benz[f]-indene-2,8'-[8H]cyclopent[g]isoquinoline]-1,1',3,5,8-pentone.

To a stirred solution of 2 mg. fredericamycin A in 5 mL of THF at room temperature was added 30 mL of ethylamine, 70% aqueous solution. The resulting blue solution was stirred at room temperature for 1 hour. The reaction mixture was concentrated under reduced pressure, and the residue redissolved in a 87:3:3 v/v/v chloroform-methanol-acetic acid solvent system, and stirred for 15 minutes. The solvents then were removed under reduced pressure to a dry residue, which on flash chromatography using 87:3:3 v/v chloroform-methanol-acetic acid as elutant afforded the title compound (2.0 mg.) as a blue solid.

$^1$H NMR (CDCl$_3$/CD$_3$OD/CF$_3$CO$_2$D, δ): 1.39 (3H, t, J=7 Hz), 1.85 (2H, d, J=7 Hz), 2.55 (2H, apparent t, J=7 Hz), 3.32 (4H, m), 5.81 (1H, s), 6.14 (3H, m), 6.44 (1H, s), 6.75 (1H, m), 6.92 (1H, s).

EXAMPLE 2

Preparation of
2',3'-Dihydro-7'-(methoxymethoxy)-1H-indene-1'-spiro-2-[4,9-dihydroxy-2H-benz[f]indene-1,3,5,8-tetrone].

Part 2A: Preparation of 4,5,8,9-tetrakis (phenylmethoxy)naphtho[2,3-c]-furan-1,3-dione.

Step 2A-a: Preparation of dimethyl 3,6-bis(phenylmethoxyl)phthalate.

14.92 g of dimethyl 3,6-dihydroxylphthalate (prepared by the methods described in Kelly, et al., J. Am. Chem. Soc., 110, 6471–6480 (1988)) was stirred at room temperature with 20 mL of benzyl bromide and 29.00 g of potassium carbonate in 230 mL of acetone for 1 day. The solid was then removed by filtration. The filtrate was concentrated and the solid was recrystallized from ethyl acetate petroleum ether to give 21.40 g of the title compound as a colorless crystal, m.p. 105°–107° C.

Step 2A-b: Preparation of dimethyl 1,4-dihydroxy-5,8-bis(phenylmethoxyl)-2,3-naphthalene dicarboxylate.

To a stirred solution of 21.31 g of dimethyl 3,6-bis(phenylmethoxyl)phthalate prepared in Step 2A-a above and 25 mL of 1,3-dimethyl-3,4,5,6-tetrahydro-2(1H)-pyrimidinone in 200 mL of THF at 0° C., was added of 290 mL of sodium bis(trimethylsilyl)amide(1M in THF). 17.0 mL of dimethyl succinate in 13 mL of THF was added via a syringe pump over a period of 2.5 hours. The reaction was allowed to warm to room temperature gradually in 4 hours before quenching with 1N HCl to pH 1 to 2. The precipitate was collected by filtration to give 9.77 g of yellow solid. The aqueous solution was extracted with ethyl acetate (3X), combined extracts were washed with brine (3X), dried over Na$_2$SO$_4$ and concentrated and the residue was purified by column chromatography eluting with 2:1 v/v ethyl acetate and petroleum ether to give an additional 7.68 g of yellow solid for a total yield of 17.45 g of the title compound.

Step 2A-c: Preparation of dimethyl 1,4,5,8-tetrakis(phenylmethoxy)-2,3-naphthalene dicarboxylate.

A mixture of 10.00 g of dimethyl 1,4-dihydroxy-5,8-bis(phenylmethoxyl)-2,3-naphthalene dicarboxylate prepared in Step 2A-b above, 12.00 g of potassium carbonate and 8.0 mL of benzyl bromide in 100 mL of dimethyl formamide and 200 mL of acetone was stirred at room temperature for 2 days. The reaction was filtered. The filtrate was then concentrated and the solid was washed with mixed solvent of ethyl acetate and petroleum ether to give 12.50 g of the title compound as a yellow solid.

Step 2A-d: Preparation of 4,5,8,9-tetrakis(phenylmethoxy)naptho-[2,3-c]furan-1,3-dione.

12.50 g of dimethyl 1,4,5,8-tetrakis(phenylmethoxy)-2,3-napthalene dicarboxylate prepared in Step 2A-c above was refluxed with 12.0 g of KOH in 24 mL of water, 300 mL of methanol and 100 mL of THF for 1 hour. The solvent was removed, and the residue acidified with 1N HCl. The solid was then collected by filtration and was refluxed in 55 mL of acetic anhydride for 30 minutes. After cooling to room temperature, a mixed solvent of 1:1 v/v diethyl ether and petroleum ether was added. The yellow crystalline solid was collected by filtration to yield 8.94 g of the title compound.

Part 2B: Preparation of 3-[7-(methoxymethoxy)-1H-indene-1-ylidene]-4,5,8,9-tetrakis(phenylmethoxy)naphtho[2,3-c]furan-1(3H-one.

To a solution of 704 mg. (4 mM) of 7-methoxymethoxyindene (prepared as described in Kelly, et al., J. Am. Chem. Soc., 110, 647 (1988)) in 20 mL of THF cooled to −78° C., was added 3.2 mL t-butyllithium (4.8 mM solution in pentane, Aldrich) dropwise under argon. The yellow solution was stirred at −78° C. for 15 minutes and then 0.73 mL of distilled trimethylsilyl chloride (5.76 mM) was added. After stirring for 15 minutes at −78°, 8 mL of NaN[Si(CH$_3$)$_3$]$_2$ (8 mM, 1.0M solution in THF, Aldrich) was added dropwise and the solution stirred for 15 additional minutes. To the resulting brownish red solution, 2.42 gm. of 4,5,8,9-tetrakis(phenylmethoxy)-naphtho[2,3-C]furan-1,3-dione (3.9 mM) in 700 mL of dry THF was added. The reaction mixture was stirred at −78° C. for 1 hour, and then 3 mL of acetic acid in 60 mL of dry methanol added, and the solution allowed to warm to room temperature. Saturated NH$_4$Cl aqueous solution was added, and the volatiles removed under reduced pressure. Ethyl ether was added and the ether layer washed with water and brine, dried (MgSO$_4$) and concentrated under reduced pressure. The crude residue was dissolved in 200 mL dry THF and treated with 20 gm. of NaOAc and 20 mL of acetic anhydride at room temperature. After stirring for 10 minutes, 40 gm. of anhydrous K$_2$CO$_3$ was added and the solution stirred for an additional 0.5 hours. The orange colored reaction mixture was poured into 300 mL ethyl ether, the ether solution washed with water and brine and dried (MgSO$_4$), and then concentrated under reduced pressure, which concentrate on flash chromatography using 30:70 v/v ethyl acetate-petroleum ether as elutant afforded the title compound (1.75 gm., 57.6%).

$^1$H NMR (CDCl$_3$, δ): 3.68 (3H, s), 5.01 (2H, s, br) 5.14 (5H, s, br), 5.25 (2H, s, br), 5.40 (2H, s, br), 6.65 (1H, d, J=5.6 Hz), 6.9–7.55 (25H, m), 7.7 (1H, d, J=5.6 Hz).

Part 2C: Preparation of 3-hydroxy-7'-(methoxymethoxy)-1H-indene-1'-spiro-2-[4,5,8,9-tetrakis(phenylmethoxy)-2H-benz[f]indene-1-one].

To 1.23 gm. (1.5 mM) of the lactone product of Part 2A above in 60 mL of dry methylene chloride cooled to −78° C., 4.94 mL diisobutylaluminum (1M in methylene chloride, Aldrich) was added over 15 minutes under argon. The reddish brown reaction mixture was stirred for 20 minutes at −78° C., and then a mixture consisting of 3 mL of acetic acid in 27 mL methylene chloride was added. The mixture was warmed to 0° C. over 10 minutes and then 30 gm. of anhydrous potassium carbonate was added. After 1 hour, the reaction solution was quenched with water and extracted with ethyl ether. The ether extracts were washed with 0.2M HCl, dried (MgSO4) and concentrated under reduced pressure to afford the title compound.

Part 2D: Preparation of 7'-(methoxymethoxy)-1H-indene-1'spiro-2-[4,5,8,9-tetrakis(phenylmethoxy)-2H-benz[f]indene-1,3-dione].

The general methods reported in Omura, et al., Tetrahedron, 34, 1651 (1978), were followed. To a solution of 3.73 mL of anhydrous dimethyl sulfoxide (56.14 mM) in 80 mL of methylene chloride at −78° C. under argon, 14.03 mL oxalyl chloride (28.07 mM, 2.0M solution in methylene chloride, Aldrich), was added dropwise over 15 minutes. After stirring for 15 minutes at −78° C., the spiroketo-alcohol reaction product of Part 2B above was added in 15 mL of anhydrous methylene chloride to the oxalyl chloride-dimethyl sulfoxide mixture over 15 minutes. The reaction mixture was stirred for 1 hour at −78° C. then 9.78 mL of freshly distilled diisopropyl ethyl amine (56.14 mM) was added dropwise over 15 minutes, the solution was stirred for an additional 15 minutes, and then warmed to 0° C. The reaction solution was quenched with water and extracted with methylene chloride, the extracts washed with water and brine and dried (MgSO4). The dried organic layer was concentrated under reduced pressure, which on flash chromatography using 1:3 ethyl acetate-petroleum ether as elutant, afforded the title compound (1.1 gm., 66%).

$^1$H NMR (CDCl$_3$, δ): 3.17 (3H, s), 4.94 (2H, s), 5.14 (2H, s), 5.15 (2H, s), 5.17 (2H, s), 5.18 (2H, s), 6.23 (1H, d, J=5.3 Hz), 6.88 (1H, d, J=8.3 Hz), 7.05 (1H, d, J=5.3HZ), 7.08 (1H, d, J=8.3 Hz), 7.19–7.32 (15H, m), 7.32–7.38 (4H, m), 7.46–7.54 (4H, m).

Part 2E: Preparation of 2',3'-Dihydro-7'-(methoxymethoxy)-1H-indene-1'-spiro-2-[4,9-dihydroxy-2H-benz[f]indene-1,3,5,8-tetrone].

To 1.0 gm. (1.31 mM) of the spiroketo reaction product of Part 2C above in a solvent of 100 mL of benzene and 150 mL of ethanol, 200 mg. of Pd/C (palladium content 10%, Aldrich) was added. The reaction mixture was stirred under an atmosphere of hydrogen and fresh catalyst (200 mg.) was added to the reaction mixture each hour over a 4 hour period. The reaction flask was then exposed to air from the ambient and stirred for 12 hours. The resultant deep-red colored reaction solution was then filtered through a short silica gel column and the elutant concentrated under reduced pressure. The resultant blue residue was taken up in methylene chloride and washed with 1M HCl aqueous solution. 15 mL of methanol was added to the solution, and the solvents then removed under reduced pressure to afford the title compound (0.52 gm., 95%) as reddish brown shiny crystals.

$^1$H NMR (CDCl$_3$, δ): 2.52 (2H, t, J=7.3 Hz), 3.19 (3H, s), 3.28 (2H, t, J=7.3 Hz), 4.86 (2H, s), 6.76 (1H, d, J=7.9 Hz), 6.98 (1H, d, J=7.9 Hz), 7.17 (2H, s), 12.83 (2H, s).

EXAMPLE 3

Preparation of 2',3'-Dihydro-7'-hydroxy-1H-indene-1'-spiro-2-[4,9-dihydroxy-benz[f]indene-1,3,5,8-tetrone].

The product of Example 2 above (10 mg.) was refluxed for 0 minutes in 5 mL of methanol with 2 drops of concentrated HCl, and then the solvent was removed under reduced pressure. The resultant residue was dissolved in methylene chloride, dried and then concentrated to yield the title compound as a red solid.

$^1$H NMR (CDCl$_3$, δ): 2.50 (2H, t, J=7.0 Hz), 3.26 (2H, t, 7.0 Hz), 6.44 (1H, apparent d, J=7.5 Hz), 6.89 (1H, apparent d, J=7.5 Hz), 7.09 (1H, apparent t, J=7.5 Hz), 7.13 (2H, s), 12.79 (2H, s).

EXAMPLE 4

Preparation of 2',3'-Dihydro-1H-indene-1'-spiro-2-[4,9-dihydroxy-2H-benz[f]-indene-1,3,5,8-tetrone].

This compound was obtained by the procedure described in Example 2 above, except 7-methoxymethoxyindene in Example 2, Part 2A was replaced with indene.

$^1$H NMR (CDCl$_3$, δ): 2.58 (2H, t, J=7 Hz), 3.03 (2H, apparent t, J=7 Hz), 6.72 (1H, apparent d, J=7 Hz), 7.08 (1H, apparent t, J=7 Hz), 7.17 (2H, s), 7.25 (1H, m), 7.34 (1H, apparent d, J=7 Hz), 12.80 (2H, s).

EXAMPLE 5

Preparation of 2',3'-Dihydro-7'-(methoxymethoxy)-6-methoxy-1H-indene-1'-spiro-2-[4,9-dihydroxy-2H-benz[f]indene-1,3,5,8-tetrone].

This compound was obtained by the procedure described in Example 2 above, except the anhydride synthon in Example 2, Part 2A was replaced with 6-methoxy-4,5,8,9-tetrakis (phenylmethoxy)naphtho[2,3,C]furan-1,3-dione.

$^1$H NMR (CDCl$_3$, δ): 2.51 (2H, t, J=7.5 Hz), 3.18 (3H, s), 3.27 (2H, t, J=7.5 Hz), 4.01 (3H, s), 4.85 (2H, s), 6.31 (1H, s), 6.74 (1H, d, J=8 Hz), 6.97 (1H, d, J=8 Hz), 7.20 (1H, t, J=8 Hz), 12.55 (1H, s), 13.19 (1H, s).

EXAMPLE 6

Preparation of 2',3'-Dihydro-7'-hydroxy-6-methoxy-1H-indene-1'-spiro-2-[4,9-dihydroxy-2H-benz[f]indene-1,3,5,8-tetrone].

This compound was obtained by hydrolysis of the product of Example 5 above. Hydrolysis was performed in a similar manner as described in Example 3 above.

$^1$H NMR (CDCl$_3$, δ) 2.51 (2H, t, J=7.5 Hz), 3.26 (2H, t, J=7.5 Hz), 4.0 (3H, s), 4.8 (1H, s, br), 6.29 (1H, s), 6.45 (1H, apparent d, J=7.5 Hz), 6.90 (1H, d, J=7.5 Hz), 7.10 (1H, apparent t, J=7.5 Hz), 12.55 (1H, s), 13.19 (1H, s).

EXAMPLE 7

Preparation of
6',7'-Dihydro-1-methoxy-9'-(methoxymethoxy)-3'-(n-pentyl)-spiro[2H-benz[f]indene-2,8'-[8H]cyclopent[g]isoquinoline]-1,3,5,8-tetrone.

Part 7A: Preparation of 6-[(tert-Butyldimethylsilyl-)oxy]-3-(n-pentyl)-2,6,7,8-tetrahydro-9-(methoxymethoxy)-1H-cyclopent[g]isoquinoline-1-one.

A solution of n-butyllithium (1.55M in hexane, 26.0 mL, 65 mM, 3.66 equiv.) was added slowly to a stirred solution of 10.9 mL (65 mM) of 2,2,6,6-tetramethylpiperidine in tetrahydrofuran at 0° C. The solution was stirred for 5 minutes at 0° C., cooled to −78° C., and then stirred for a further 5 minutes. To this solution was added 7.49 gm. (17.76 mM) 1-[(t-butyldimethylsilyl)oxy]-N,N,-diethyl-2,3-dihydro(methoxy-methoxy-6-methyl-1H-indene-5-carboxamide (prepared as described in Kelly, et al., *J. Am. Chem. Soc.*, 110, 6471 (1988)) in 60 mL of THF. The resulting solution was stirred for 15 minutes at −78° C., and then 7.8 mL (65 mM) of 1-cyanopentane added and the reaction mixture stirred for a further 10 minutes at −78° C., followed by 5 minutes at room temperature. The reaction mixture was quenched with 1M HCl and diluted with ether; the organic phase washed with saturated $NH_4Cl$ and NaCl and then dried ($Na_2SO_4$) The solvent was removed and the concentrate washed with diethyl ether to afford 0.74 g of the title compound. The diethyl ether washings use concentrated, and the resultant residue purified by column chromatography eluting with 1:1 v/v ethyl acetate and petroleum ether to give additional 4.01 g of product. Total yield 4.75 g (60%).

Part 7B: Preparation of 6-hydroxy-3-(n-pentyl)-2,6,7,8-tetrahydro-9-(methoxymethoxy)-1H-cyclopent[g]isoquinolin-1-one.

To a solution of 4.01 gm. of the product of Part 7A above in 30 mL of THF at 0° C. was added a solution of n-$Bu_4NF$ (Aldrich, 1M in THF, 9.0 mL, 9.0 mM); the ice bath was then removed and the reaction mixture stirred at room temperature for 1.5 hours. The reaction mixture was then diluted with ethyl acetate, washed with saturated NaCl, dried ($NaSO_4$), and the solvent removed. The resulting crude product was purified by recrystallization from diethyl ether and petroleum ether to give 0.49 gm. of the title compound. The mother liquid was concentrated, and resultant residue purified by column chromatography on silica gel eluting with ethyl acetate to give additional 0.64 g of title compound and a total yield of 1.13 g.

Part 7C: Preparation of 3-(n-pentyl)-9-(methoxymethoxy)-1,2-dihydro-8H-cyclopent[g]isoquinolin-1-one.

To a stirred solution of 537 mg. (1.62 mM) of the product of Part 7B above and 736 mg. (3.24 mM) of o-nitrophenyl selenocyanate in 20 mL of THF was added 0.807 mL (3.24 mM) of tri-n-butylphosphine dropwise over approximately 10 minutes. The reaction was stirred at room temperature for 1.5 hours, after which time thin layer chromatography indicated complete formation of the selenide. The reaction was then cooled to 0° C., and 0.80 mL of hydrogen peroxide (30 wt. % in $H_2O$) was added dropwise. The reaction mixture was allowed to slowly warm to room temperature over a period of 2 hours, and the reaction mixture was then diluted with ether, washed with brine (4x), dried over $MgSo_4$ and concentrated. The crude product was purified by column chromatography on silica gel eluting with 1:1 v/v ethyl acetate and petroleum ether to give 324 mg. of product as a pale yellow solid.

Part 7D: Preparation of 1-Methoxy-3-(n-pentyl)-9-(methoxymethoxy)-8H-cyclopent[g]isoquinoline.

1.43 gm. (5.19 mM) of silver carbonate and 0.35 mL (5.62 mM) of methyl iodide were added to a solution of the reaction of Part 7C above in 20 mL of benzene. The mixture was sonicated in the dark for 4 days under argon, and then filtered through a pad of Celite, washed with benzene, and then filtered through a plug of silica gel to afford the title compound as an oil.

Part 7E: The title compound of Example 7 was synthesized by the procedures of Example 2 above, replacing 7-methoxymethoxyindene in Example 2, Part 2A with the indene reaction product of Part 7D above.

$^1$H NMR (CDCl$_3$, δ): 0.90 (3H, t, J = 7 Hz), 1.34 (4H, m), 1.78 (2H, m), 2.53 (2H, t, J = 7 Hz), 2.70 (2H, t, J = 7 Hz), 2.98 (3H, s), 3.40 (2H, t, J = 7 Hz), 3.99 (3H, s), 4.82 (2H, s), 6.90 (1H, s), 7.15 (2H, s), 7.38 (1H, s).

EXAMPLE 8

Preparation of
2',6',7'-Trihydro-4,9,9'-trihydroxy-3'-(n-pentyl)-spiro[2H-benz[f]-indene-2,8'-[8H]cyclopent[g]isoquinoline]-1,1',3,5,8-pentone.

900 mg. of toluenesulfonic acid monohydrate and 2.18 g of NaBr was added to a solution of 119.7 mg. of the product of Example 7 above in 80 mL of methanol. The mixture was refluxed for 1.5 hours, cooled to room temperature diluted with 200 mL of ethyl acetate. The solution was then washed twice with saturated NaHCO$_3$ solution, twice with water, one time with brine solution, and then dried (MgSO$_4$) and concentrated under reduced pressure. The crude product upon flash chromatography using 87:3:3 v/v chloroform-methanol-acetic acid afforded the title compound in almost quantitative yield as a brownish red solid.

$^1$HNMR (CDCl$_3$/CD$_3$OD, δ): 0.70 (3H, t, J = 7 Hz), 1.16 (4H, m), 1.47 (2H, m), 2.31 (2H, t, J = 7 Hz), 2.37 (2H, t, J = 7 Hz), 3.15 (2H, t, J = 7 Hz), 6.11 (1H, s), 6.72 (1H, s), 7.0 (2H, s). Mass spectrum; m/e 515 (M+2).

EXAMPLE 9

Preparation of
6',7'-Dihydro-1-methoxy-9'-(methoxymethoxy-3-(diethoxymethyl)-spiro[2H-benz[f]indene-2,8'-8H]cyclopent[g]isoquinoline]-1,3,5,8-tetrone.

The title compound was obtained by the procedure described in Example 2 above, except the indene employed in Example 2, Part 2A was substituted with 3-diethoxymethyl-1-methoxy-9-(methoxymethoxy)-H-cyclopent[g]isoquinoline, (JACS, 110, 6471 (1988)).

$^1$H NMR (CDCl$_3$, δ) 1.27 (6H, t, J = 7 Hz), 2.56 (2H, t, J = 7 Hz), 2.99 (3H, s), 3.41 (2H, t, J = 7 Hz), 3.66 (4H, m), 4.03 (3H, s), 4.82 (2H, s), 5.43 (1H, s), 7.16 (2H, s, br), 7.45 (1H, s), 7.51 (1H, s), 12.85 (2H, s, br).

EXAMPLE 10

Preparation of
6',7'-Dihydro-1-methoxy-9'-(methoxymethoxy)-3'-formylspiro[2H-benz[f]indene-2,8'-[8H]cyclopent[g]isoquinoline]-1,3,5,8-tetrone.

20 mg. of the product of Example 9 above was stirred in 15 mL of 1:1:1 v/v tetrahydrofuran-acetone-0.015 N HCl at room temperature for 1.5 hours. The reaction mixture was diluted with ethyl acetate, dried (MgSo$_4$)

and concentrated. The crude product was purified by preparative thin layer chromatography (EtOAC with 0.5% AcOH) to afford the title compound (5 mg.).

$^1$H NMR (CDCl$_3$, δ): 2.60 (2H, t, J=7.4 Hz), 2.99 (3H, s), 3.46 (2H, apparent t), 4.12 (3H, s), 4.84 (2H, s), 7.18 (2H, s, br), 7.67 (1H, s), 7.88 (1H, s), 10.03 (1H, s) 12.81 (2H, s, br).

EXAMPLE 11

Preparation of 2',3'-Dihydro-6-ethylamino-7'-(methoxymethoxy)-1H-indene-1'-spiro-2-[4,9-dihydroxy-2H-benz[f]-indene-1,3,5,8-tetrone].

To a stirred solution of 20 mg. of the quinone product of Example 2 in 5 mL of THF, there was added approximately 0.5 mL of 70% ethylamine, aqueous solution. The reaction mixture was stirred for 2 hours with exposure to air from the ambient, then concentrated under reduced pressure to a solid residue, which on flash chromatography using 94:3:3 v/v methylene chloride-methanol-acetic acid as elutant afforded the title compound (18.1 mg.) as a brownish red solid.

$^1$H NMR (CDCl$_3$, δ): 1.40 (3H, t, J=7 Hz), 2.51 (2H, t, J=7 Hz), 3.19 (3H, s), 3.24 (2H, t, J=7 Hz), 3.31 (2H, m), 4.87 (1H, d, J=6.5 Hz), 4.84 (1H, d, J=6.5 Hz), 5.82 (1H, s), 6.19 (1H, m), 6.75 (1H, dd, J$_1$=7 Hz, J$_2$=0.7 Hz), 6.97 (1H, dd, J=7.5 Hz, J$_2$=0.7 Hz), 7.20 (1H, t, J=7.5 Hz), 12.18 (2H, s).

EXAMPLES 12-23

By procedures similar to those employed in Example 11 but replacing ethylamine with the appropriate amine, the following compounds were prepared having the following spectral characteristics:

EXAMPLE 12

2',3'-Dihydro-6-methylamino-7'-(methoxymethoxy)-1H-indene-1'-spiro-2-[4,9-dihydroxy-2H-benz[f]-indene-1,3,5,8-tetrone].

$^1$HNMR (CDCl$_3$/CD$_3$OD, δ): 2.51 (2H, t, J=7 Hz), 3.01 (3H, d, J=5.4 Hz), 3.19 (3H, s), 3.27 (3H, t, J=7 Hz), 4.86 (1H, d, J=6.6 Hz), 4.88 (1H, d, J=6.6 Hz), 5.80 (1H, s), 6.76 (1H, dd, J$_1$=7.5 Hz, J$_2$=0.8 Hz), 6.98 (1H, dd, J$_1$=7.5 Hz, J$_2$=0.8 Hz), 7.22 (1H, t, J=7.5 Hz).

EXAMPLE 13

2',3'-Dihydro-6-(2,2,2-trifluoroethylamino)-7'-(methoxymethoxy)-1H-indene-1'-spiro-2-[4,9-dihydroxy-2H-benz[f]-indene-1,3,5,8-tetrone].

$^1$H NMR (CDCl$_3$/CD$_3$OD, δ) 2.51 (2H, t, J=7 Hz), 3.19 (3H, s), 3.27 (2H, t, J=7 Hz), 3.95 (2H, q, J=8.5 Hz), 4.86 (1H, d, J=7 Hz), 4.89 (1H, d, J=7 Hz), 6.05 (1H, s), 6.76 (1H, dd, J$_1$=7.5 Hz, J$_2$=0.8 Hz), 6.99 (1H, dd, J$_1$=7.5 Hz, J$_2$=0.8 Hz), 7.22 (1H, t, J=7.5 Hz).

EXAMPLE 14

6-amino-2',3'-dihydro-7'-(methoxymethoxy)-1H-indene-1'-spiro-2-[4,9-dihydroxy-2H-benz[f]-indene-1,3,5,8-tetrone].

$^1$H NMR (CDCl$_3$/CD$_3$OD, δ): 2.51 (2H, t, J=7 Hz), 3.20 (3H, s), 3.27 (2H, t, J=7 Hz), 4.86 (1H, d, J=6.7 Hz), 4.89 (1H, d, J=6.7 Hz), 6.04 (1H, s), 6.76 (1H, dd, J$_1$=7.5 Hz, J$_2$=0.7 Hz), 6.98 (1H, dd, J$_1$=7.5 Hz, J$_2$=0.7 Hz), 7.22 (1H, t, J=7.5 Hz).

EXAMPLE 15

2',3'-Dihydro-6-ethylamino-7'-hydroxy-1H-indene-1'-spiro-2-[4,9-dihydroxy-2H-benz[f]-indene-1,3,5,8-tetrone].

$^1$HNMR (CDCl$_3$/CD$_3$OD, δ): 1.37 (3H, t, J=7 Hz), 2.47 (2H, t, J=7 Hz), 3.23 (2H, t, J=7 Hz), 3.34 (2H, q, J=7 Hz), 5.80 (1H, s), 6.52 (1H, dd, J$_1$=7.5 Hz, J$_2$=0.7 Hz), 6.82 (1H, dd, J$_1$=7.5 Hz, J$_2$=0.7 Hz), 7.09 (1H, t, J=7.5 Hz).

EXAMPLE 16

2',3'-Dihydro-7'-(methoxymethoxy)-1H-indene-1'-spiro-[4,9-dihydroxy-6-(2-hydroxyethylamino)-2H-benz[f]indene-1,3,5,8-tetrone].

$^1$HNMR (CDCl$_3$, δ): 2.51 (2H, t, J=7 Hz), 3.19 (3H, s), 3.27 (2H, t, J=7 Hz), 3.43 (2H, m), 3.97 (2H, m), 4.85 (2H, m), 5.85 (1H, s), 6.63 (1H, m), 6.74 (1H, d, J=7.6 Hz), 6.97 (1H, d, J=7.6 Hz), 7.20 (1H, t, J=7.6 Hz), 12.19 (1H, s), 14.09 (1H, s).

EXAMPLE 17

2',3'-Dihydro-7'-(methoxymethoxy)-1H-indene-1'-spiro-2-[6-(2-hydroxy-2-phenyl-ethylamino)-4,9-dihydroxy-2H-benz[f]indene-1,3,5,8-tetrone].

1H NMR (CDCl$_3$, δ): 2.5 (2H, apparent t, J=7 Hz), 3.16 (3H, s), 3.26 (2H, apparent t, J=7 Hz), 3.49 (2H, m), 4.85 (2H, s, br), 5.04 (1H, m), 5.82 (1H, s, br), 6.44 (1H, apparent d, J=7 Hz), 6.96 (1H, apparent d, J=7 Hz), 7.20 (1H, apparent t, J=7 Hz), 7.40 (6H, m), 12.16 (1H, s, br), 14.08 (1H, s, br).

EXAMPLE 18

2',3'-Dihydro-7'-(methoxymethoxy)-1H-indene-1,-spiro-2-[6-(phenylamino)-4,9-dihydroxy-2H-benz[f]indene-1,3,5,8-tetrone].

$^1$HNMR (CDCl$_3$, δ): 2.52 (2H, t, J=7 Hz), 3.20 (3H, s), 3.27 (2H, t, J=7 Hz), 4.86 (2H, m), 6.43 (1H, s), 6.68 (1H, d, J=7.6 Hz), 6.76 (1H, d, J=7.6 Hz), 6.98 (1H, d, J=7.6 Hz), 7.15 (1H, d, J=7.6 Hz), 7.21 (1H, t, 7.6 Hz), 7.32 (2H, t, J=7.6 Hz), 7.49 (2H, t, J=7.6 Hz), 7.83 (1H, s), 13.94 (2H, s).

EXAMPLE 19

2',3'-Dihydro-7'-(methoxymethoxy)-1H-indene-1'-spiro-2-[6-(4-carboxyanilino)-4,9-dihydroxy-2H-benz[f]indene-1,3,5,8-tetrone].

$^1$H NMR (CDCl$_3$/CD$_3$OD, δ): 2.45 (2H, apparent t, J=7.6 Hz), 3.13 (3H, s), 3.21 (2H, apparent t, J=7.6 Hz), 4.8 (2H, s, br), 6.51 (1H, s, br), 6.70 (1H, apparent d, J=7.8 Hz), 6.91 (1H, apparent d, J=7.8 Hz), 7.15 (1H, apparent t, J=7.8 Hz), 7.32 (2H, apparent d, J=8.5 Hz), 8.1 (2H, apparent d, J=8.5 Hz).

EXAMPLE 20

2',3'-Dihydro-7'-(methoxymethoxy)-1H-indene-1,-spiro-2-[6-(3-carboxyanilino)-4,9-dihydroxy-2H-benz[f]indene-1,2,5,8-tetrone].

$^1$H NMR (CDCl$_3$, δ): 2.53 (2H, apparent t, J=7 Hz), 3.20 (3H, s), 3.27 (2H, apparent t, J=7 Hz), 4.88 (2H, m), 6.46 (1H, s), 6.76 (1H, apparent d, J=7.8 Hz), 6.98 (1H, apparent d, J=7.8 Hz), 7.21 (1H, apparent t, J=7.8 Hz), 7.52-7.66 (2H, m), 7.88 (1H, s), 8.04 (2H, s, br), 12.20 (1H, br), 13.82 (1H, s).

EXAMPLE 21

2',3'-Dihydro-7'-(methoxymethoxy)-1H-indene-1'-spiro-2-[6-(4-hydroxyanilino)-4,9-dihydroxy-2H-benz[f]indene-1,3,5,8-tetrone].

$^1$H NMR (CDCl$_3$, δ): 2.5 (2H, apparent t, J=7 Hz), 3.19 (3H, s), 3.26 (2H, apparent t, J=7 Hz), 4.86 (2H, m), 6.24 (1H, s), 6.67 (1H, apparent d, J=10 Hz), 6.9–7.0 (3H, m), 7.12–7.24 (3H, m), 7.7 (1H, s, br), 12.42 (1H, s, br), 13.8 (2H, s, br).

EXAMPLE 22

6',7'-Dihydro-4,9-dihydroxy-6-ethylamino-1'-methoxy-9'-(methoxymethoxy)-3'-(n-pentyl)-spiro[2H-benz[f]indene-2,8'[8H]cyclopent[g]isoquinoline]-1,3,5,8-tetrone.

$^1$H NMR (CDCl$_3$/CD$_3$OD, δ): 0.70 (3H, t, J=7 Hz), 1.16 (4H, m), 1.47 (2H, m), 2.31 (2H, t, J=7 Hz), 2.37 (2H, t, J=7 Hz), 3.15 (2H, t, J=7 Hz), 6.11 (1H, s), 6.72 (1H, s), 7.00 (2H, s, br).

EXAMPLE 23

2',6'7'-trihydro-4,9,9'-trihydroxy-3'-(n-pentyl)-6-ethylamino-spiro[2H-benz[f]-indene-2,8'-[8H]cyclopent[g]-isoquinoline]-1,1',3,5,8-pentone.

$^1$H NMR (CDCl$_3$/CD$_3$OD, δ): 0.70 (3H, t, J=7 Hz), 1.16 (4H, m), 1.47 (2H, m), 2.31 (2H, t, J=7 Hz), 2.37 (2H, t, J=7 Hz), 3.15 (2H, t, J=7 Hz), 6.11 (1H, s), 6.72 (1H, s), 7.00 (2H, s, br).

EXAMPLE 24

2',3'-Dihydro-7'-hydroxy-1H-indene-1'-spiro-2-[6-(2-(dimethylamino)ethyl)-4,9-dihydroxy-2H-benz[f]indene-1,3,5,8-tetrone] hydrochloride.

A few drops of N,N-dimethylethylene diamine was added to a stirred solution of 23 mg. of the quinone product of Example 2 in 5 mL of THF at room temperature. After 20 minutes, the reaction mixture was concentrated under reduced pressure to a blue residue, which on flash chromatography using 2:2:0.5:0.5 v/v methylene chloride-methanol-acetic acid-H$_2$O as elutant gave a blue solid. This solid was then dissolved in 2N HCl in methanol solution and refluxed for 1 hour. The solution was then concentrated under reduced pressure to a red solid, which on passing through pad of ion exchange resin (Dowex ® 1×2-400) and lyophilization afforded the title compound (22.6 mg.) as a dark red cotton-like solid.

$^1$HNMR (DMSO/D$_2$O, δ): 2.32 (2H, t, J=7 Hz), 2.82 (6H, s), 3.06 (2H, t, J=7 Hz), 3.35 (4H, m), 5.95 (1H, s), 6.53 (1H, d, J=7 Hz), 6.78 (1H, d, J=7), 7.07 (1H, t, J=7 Hz).

EXAMPLE 25

Preparation of 6-(2-(dimethylamino)ethyl)-2',6',7'-trihydro-4,9,9'-trihydroxy-3'-(n-pentyl)-spiro[2H-benz[f]-indene-2,8'-[8H]cyclopent[g]isoquinoline]1,1',3,5,8-pentone hydrochloride.

By procedures similar to those employed in Example 24 and replacing the quinone product of Example 2 with the product of Example 7, the title compound was prepared having the following spectral characteristics:

$^1$H NMR (DMSO/D$_2$O, δ): 0.80 (3H, m), 1.22 (4H, m), 1.57 (2H, m), 2.50 (2H, m), 2.82 (8H, m), 3.16 (m, 2H), 3.37 (4H, m), 5.95 (1H, s), 6.70 (1H, s), 6.88 (1H, s).

EXAMPLE 26

Preparation of 2',3'-Dihydro-7'-(methoxymethoxy)-1H-indene-1'-spiro-2-4,9-dihydroxy-6-(1-carboxy-2-carbamoylethylamino)-2H-benz[f]indene-1,3,5,8-tetrone.

To a stirred solution of 10 mg. (0.0238 mM) of the quinone product of Example 2 above in 5 mL of dimethylformamide was added approximately 1.5 mL of 0.1N aqueous solution of L-Asparagine sodium salt. After 0.5 hours, the reaction mixture was diluted with methylene chloride, the solution washed with 1 N HCl twice and water once, and dried (MgSO$_4$). The reaction mixture was then concentrated under reduced pressure to a red residue, which on flash chromatography using 100:10:5 v/v methylene chloride-methanol-acetic acid as elutant afforded the title compound (6.4 mg.) as a dark red solid.

$^1$HNMR (CDCl$_3$/CD$_3$OD, δ): 2.51 (2H, t, J=7), 2.80 (2H, m), 3.27 (2H, t, J=7 Hz), 3.65 (1H, m), 3.19 (3H, s), 4.45 (1H, s, br) 5.89 (1H, s), 6.75 (1H, d, J=7 Hz), 6.98 (1H, d, J=7 Hz), 7.21 (1H, t, J=7 Hz).

EXAMPLE 27

Preparation of 6-((2',3'-dihydro-7'-(methoxymethoxy)-1H-indene-1'-spiro-[4,9-dihydroxy-2H-benz[f]indene-1,3,5,8-tetrone]-6-yl)amino)penicillanic acid.

By procedures similar to those employed in Example 26, the title compound was prepared as a mixture of diastereomers having the following spectral characteristics:

$^1$HNMR (CDCl$_3$, δ): 1.65, 1.66 (3H, two s), 1.69, 1.70 (3H, two s), 2.51, 2.52 (2H, two t, J=7 Hz), 3.190, 3.193 (3H, two s), 3.27 (2H, t, J=7 Hz), 4.58 (1H, s), 4.86 (2H, s), 5.09 (1H, dd, J$_1$32 7.5 Hz, J$_2$=4 Hz), 5.76, 5.77 (1H, two d, J=4 Hz), 6.08, 6.09 (1H, two s), 6.75 (1H, d, J=7.5 Hz), 6.82, 6.84 (1H, two d, J=7.5 Hz), 6.97 (1H, d, J=7.5 Hz), 7.21 (1H, t, J=7.5 Hz), 12.15 (1H, s, br), 13.74, 13.75 (2H, two s).

EXAMPLE 28

Preparation of 2',3'-dihydro-7'-hydroxy-1H-indene-1'-spiro-2-[6(1-carboxy-4-((guanidinobutyl)amino)-4,9-dihydroxy-2H-benz[f]indene-1,3,5,8-tetrone].

To a stirred solution of 20 mg. of the quinone product of Example 2 above in 3 mL of THF and 10 mL of methanol was added a molar excess of an L-Arqinine solution, the solution prepared by dissolving L-Arqinine hydrochloride in H$_2$O and adding triethylamine to a pH of between about 10 to 11. The resulting solution was stirred at about 20° C. for 2 hours and then concentrated under reduced pressure. The resulting residue was redissolved with heated 2N HCl methanol solution, and concentrated under reduced pressure to a red solid, which was dissolved in a 100:25:20 v/v methylene chloride-methanol-acetic acid solution, and filtered through a sindered glass funnel. The filtrate was concentrated under reduced pressure and the residue was purified twice by flash chromatography using 100:20:5:3 v/v methylene chloride-methanol-acetic acid-water as elutant to afford the title compound (24.5 mg.) as a dark red solid.

$^1$H NMR (CD$_3$OD, δ): 2.10 (2H, m), 2.45 (2H, m), 3.25 (24H, m), 4.40 (1H, m), 5.87 (1H, apparent s), 6.51

(1H, apparent d, J=7 Hz), 6.80 (1H, apparent d, J=7 Hz), 7.09 (1H, apparent t, J=7 Hz).

EXAMPLE 29

Preparation of
2′,3′-Dihydro-7′-(methoxymethoxy)-1H-indene-1′-spiro-2-[6-((carboxymethyl)amino)-4,9-dihydroxy-2H-benz[f]indene-1,3,5,8-tetrone]sodium salt.

8 mg. of $H_2NCH_2CO_2Na \cdot XH_2O$ in 1 mL of $H_2O$ was added to 20.0 mg. of the quinone product of Example 2 above in a 2:3 v/v methylene chloride-methanol solution. The blue solution was stirred at about 20° C. for 2 hours. The solution was then concentrated under reduced pressure to a residue, which on passing through pad of ion exchange resin (Bio-Rex 70, sodium form, 200–400 mesh) and lyophilization afforded the title compound (23.2 mg.) as a blue cotton-like solid.

$^1$HNMR ($D_2O$, δ): 2.50 (2H, t, J=7 Hz), 3.17 (3H, s), 3.23 (2H, t, J=7 Hz), 3.43 (2H, s), 4.85 (2H, m), 5.90 (1H, s), 6.75 (1H, apparent d, J=7 Hz), 6.98 (1H, apparent d, J=7 Hz), 7.21 (1H, apparent t, J=7 Hz).

EXAMPLE 30

Preparation of
2,3′-Dihydro-7′-(methoxymethoxy)-1H-indene-1′-spiro-2-[6,7-di(ethylmercapto)-4,9-dihydroxy-2H-benz[f]indene-1,3,5,8-tetrone.

Four drops of ethanethiol (molar excess) was added to a solution of 34.9 mg. of the quinone product of Example 2 above in 0.5 mL of methanol and 5 mL of methylene chloride at room temperature. After stirring for 20 hours at room temperature, the reaction mixture was concentrated under reduced pressure to a residue, which on flash chromatography using 100:1.5:1.5 v/v methylene chloride-methanol-acetic acid as elutant afforded the title compound (14.4 mg.) as a dark red solid.

$^1$H NMR (CDCl$_3$, δ): 1.38 (6H, t, J=7 Hz), 2.50 (2H, t, J=7 Hz), 3.19 (3H, s), 3.27 (2H, t, J=7 Hz), 3.43 (4H, q, J=7 Hz), 4.86 (2H, s), 6.76 (1H, dd, J$_1$=7.5 Hz, J$_2$=0.6 Hz), 6.97 (1H, dd, J$_1$=7.5 Hz, J$_2$=0.6 Hz), 7.21 (1H, t, J=7.5 Hz), 12.92 (2H, s).

EXAMPLE 31–32

By procedures similar to those employed in Example 30, the following compounds were prepared having the following spectral characteristics:

EXAMPLE 31

2′,3′-Dihydro-7′-(methoxymethoxy)-1H-indene-1′-spiro-2-[6,7-di(phenylmercapto)-4,9-dihydroxy-2H-benz[f]indene-1,3,5,8-tetrone].

$^1$HNMR (CDCl$_3$, δ): 2.47 (2H, t, J=7 Hz), 3.18 (3H, s), 3.25 (2H, t, J=7 Hz), 4.86 (2H, s), 6.74 (1H, dd, J$_1$=7.5 Hz, J$_2$=0.7 Hz), 6.96 (1H, dd, J$_1$=7.5 Hz, J$_2$=0.7 Hz), 7.20 (1H, t, J=7.5 Hz), 7.32 (10H, m), 12.29 (2H, s, br).

EXAMPLE 32

2′,3′-Dihydro-7′-hydroxy-1H-indene-1′-spiro-2-[4,9-dihydroxy-6,7-di(phenylmercapto)-2H-benz[f]indene-1,3,5,8-tetrone].

$^1$HNMR (CDCl$_3$, δ): 2.45 (2H, t, J=7 Hz), 3.22 (2H, t, J=7 Hz), 6.42 (1H, t, J=7 Hz), 6.87 (1H, d, J=7 Hz), 7.06 (1H, t, J=7 Hz), 7.34 (10H, m), 12.25 (2H, s, br).

EXAMPLE 33

Preparation of
2′,3′-Dihydro-7′-(methoxymethoxy)-1H-indene-1′-spiro-2-[4,9-dihydroxy-6-(2-hydroxyethylmercapto)-2H-benz[f]indene-1,3,5,8-tetrone].

To a solution of 20 mg. of the quinone product of Example 2 above in 3 mL of methylene chloride at −5° C. was added 3.6 μL of 2-mercaptoethanol. After stirring for 45 minutes at −5° C., 5 mg. of benzoquinone was added and a red coloration of the reaction solution observed. The reaction mixture was stirred for 15 minutes under nitrogen and then a further 15 minutes with exposure to air from the ambient. The reaction mixture was concentrated under reduced pressure to a residue, which on flash chromatography using 98:1:1 methylene chloride-acetic acid-methanol as elutant afforded the title compound (11 mg.) as a dark red solid.

$^1$HNMR (CDCl$_3$, δ) 2.51 (2H, t, J=7.3 Hz), 3.18 (5H, m), 3.27 (2H, t, J=7 Hz), 4.02 (2H, m), 4.86 (2H, s), 6.74 (1H, d, J=7 Hz), 6.85 (1H, s), 6.97 (1H, d, J=7.5 Hz), 7.21 (1H, t, J=7.5 Hz), 12.51 (1H, s), 13.15 (1H, s).

EXAMPLE 34

Preparation of
2′,3′-Dihydro-7′-(methoxymethoxy)-1H-indene-1′-spiro-2-[4,9-dihydroxy-6-(phenylmercapto)-2H-benz[f]indene-1,3,5,8-tetrone].

By procedures similar to those employed in Example 33, the title compound was prepared having the following spectral characteristics:

$^1$H NMR (CDCl$_3$, δ) 2.51 (2H, t, J=7.3 Hz), 3.18 (3H, s), 3.27 (2H, t, J=7.3 Hz), 4.85 (2H, s), 6.21 (1H, s), 6.74 (1H, d, J=7.8 Hz), 6.97 (1H, d, J=8 Hz), 7.21 (1H, t, J=8 Hz), 7.57 (5H, s, br), 12.54 (1H, s), 13.09 (1H, s).

EXAMPLE 35

Preparation of
2′,3′-Dihydro-7′-hydroxy-1H-indene-1′-spiro-2-[4,9-dihydroxy-6-(2(2-aminoethyldithio)ethylamino)-2H-benz[f]indene-1,3,5,8-tetrone] hydrochloride.

To a solution cooled to 0° C. of 21.4 mg. (0.18 mM) of cystamine dihydrochloride in 0.5 mL water and 1 mL methanol was added 7 μL triethylamine. 20 mg. of the quinone product of Example 2 above was added and the reaction mixture diluted with 2 mL methanol and 2 mL methylene chloride. The reaction solution was concentrated under reduced pressure to a residue, which was purified by flash chromatography using 80:16:2:2 v/v methylene chloride-methanol-acetic acid-H$_2$O as elutant. The product was then dissolved in a 2N HCl methanol solution stirred for 8 hours at room temperature to form the hydrochloride salt of the primary amine. The solution was then concentrated under reduced pressure to a residue, which on flash chromatography using 80:16:2:2 v/v methylene chloride-methanol-acetic acid-H$_2$O as elutant afforded the title compound.

$^1$HNMR (CDCl$_3$, CD$_3$OD, δ): 2.35 (apparent t, 2H), 2.95 (2H, apparent t), 3.12 (2H, apparent t), 3.25 (2H, apparent t) 3.6 (2H, apparent t), 3.8 (2H, apparent t), 5.8 (1H, s, br), 6.45 (1H, d, J=7.5 Hz), 6.7 (1H, d, J=7.5 Hz), 7.0 (1H, t, J=7.5 Hz).

EXAMPLE 36

Preparation of
2',3'-Dihydro-7'-(methoxymethoxy)-1H-indene-1'-spiro-2-[4,9-dihydroxy-6-(4-(4-aminophenyldithio)-phenylamino)-2H-benz[f]indene-1,3,5,8-tetrone].

To a solution of 20 mg. (0.08 mM) of 4-aminophenyl disulfide in 3 mL of methanol (3 mL) was added 20 mg. of the quinone prepared in Example 2 above in 2 mL of methylene chloride. The reaction mixture was stirred at about 20° C. for 48 hours. The solvent was removed under reduced pressure, which on flash chromatography using 98:1:1 v/v methylene chloride-methanol-acetic acid as elutant afforded the title compound as a dark blue solid.

$^1$HNMR (CDCl$_3$, δ) 2.5 (2H, t, J=7.2 Hz), 3.19 (3H, s) 3.26 (2H, t, J=7.2 Hz), 4.86 (2H, m), 6.42 (1H, s), 6.6 (2H, d, J=8.5 Hz), 6.74 (1H, d, J=8 Hz), 6.96 (1H, d, J=8 Hz), 7.17–7.37 (5H, m), 7.6 (2H, d, J=8.5 Hz), 7.82 (1H, s), 13.82 (1H, s), 13.91 (1H, s).

EXAMPLES 37–82

By using the procedures described in Example 11 above and appropriate amines, compounds of the below formula and shown in Table I can be prepared.

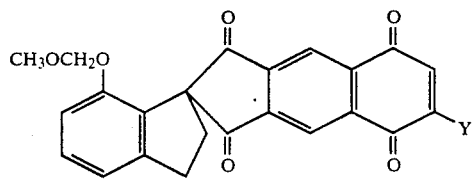

TABLE I

| Ex. No. | Y |
|---|---|
| 37 | —N(CH$_3$)$_2$ |
| 38 | —NHYCH$_2$CH$_2$CH$_3$ |
| 39 | —NH—cyclopropyl |
| 40 | —NH—cyclopentyl |
| 41 | —NH—cyclohexyl |
| 42 | —N(aziridine) |
| 43 | —N(pyrrolidine) |
| 44 | —N(piperidine) |
| 45 | —NHCH$_2$CH=CH$_2$ |
| 46 | —NHCH$_2$C(CH$_{23}$)=CH$_2$ |
| 47 | —NHCH$_2$(CL)=CH$_2$ |
| 48 | —NHCH$_2$C≡CH |
| 49 | —NHC(CH$_3$)$_2$C≡CH |
| 50 | —N(CH$_3$)CH$_2$C≡CH |
| 51 | —NHCH$_2$CH$_2$OH |
| 52 | —NHCH$_2$CH$_2$CH$_2$OH |
| 53 | —NHCH$_2$C$_6$H$_5$ |
| 54 | —NHCH$_2$-(pyridyl) |
| 55 | —NH-(N-methylimidazolyl) |
| 56 | —NH-(thiazolyl) |
| 57 | —NH-(furyl) |
| 58 | —NH-(thienyl) |
| 59 | —NH-(4-fluorophenyl) |
| 60 | —NH-cyclohexyl |
| 61 | —NH-(pyridyl) |
| 62 | —N(N'-methylpiperazinyl) |
| 63 | —N(3-aminopyrrolidinyl) |
| 64 | —N(3-hydroxypyrrolidinyl) |
| 65 | —N(3,4-dihydroxypyrrolidinyl) |

TABLE I-continued

| Ex. No. | Y |
|---|---|
| 66 | -N (pyrroline ring) |
| 67 | -N (imidazole ring) |
| 68 | -N (morpholine ring, O) |
| 69 | -NH-C₆H₄-NH₂ |
| 70 | -NH-C₆H₄-N(CH₃)₂ |
| 71 | -NH-(pyrrolidine)-NH |
| 72 | -NH(CH₂)₂S-S-CH₂C₆H₅ |
| 73 | -NH(CH₂)₂S-S-C₆H₅ |
| 74 | -NH(CH₂)₂S-S-(CH₂)₂OH |
| 75 | -NH(CH₂)₂S-S-CH₂-(N-methylimidazole) |
| 76 | -NH(CH₂)₂S-S-(4-pyridyl) |
| 77 | -NH(CH₂S-S-(CH₂)₂NH₂ |
| 78 | -NH(CH₂)₂(S)₂(CH₂)₂NHCOCH₃ |
| 79 | -NH(CH₂)₂S-S-C₆H₄-F |
| 80 | -NH(CH₂)₂S-S-C₆H₃(F)(F) (2,4-difluoro) |
| 81 | -NH(CH₂)₂S-S-C₆H₄-NH₂ |
| 82 | -NH(CH₂)₂S-S-C₆H₄-NO₂ |

EXAMPLES 83 to 148

By using the procedures described in Example 1 above and appropriate amines, compounds of the below formula and shown in Table II can be prepared.

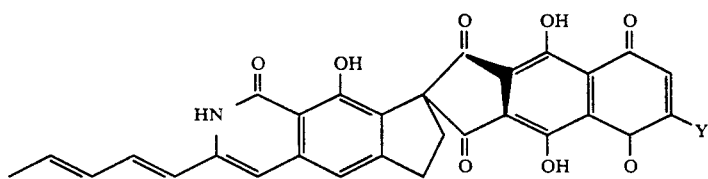

TABLE II

| Ex. No. | Y |
|---|---|
| 83 | -NH₂ |
| 84 | -NHCH₃ |
| 85 | -NHCH₂CF₃ |
| 86 | -NH(CH₂)₂CH₃ |
| 87 | -N(CH₃)₂ |
| 88 | -NH(CH₂)₂OH |
| 89 | -NH(CH₂)₃OH |
| 90 | -NH(CH₂)₂Cl |
| 91 | -NH(CH₂)₃Cl |
| 92 | -NHCH₂C(=O)NH₂ |
| 93 | -NH(CH₂)₂N(CH₃)₂ |
| 94 | -NHCH₂COOH |
| 95 | -NHCH(COOH)CH₂C(=O)NH₂ |
| 96 | -NH(COOH)(CH₂)₄N(=NH)NH₂ |
| 97 | -NH-(β-lactam with S-C(CH₃)₂ and N-CH-COOH) |
| 98 | -NHCH₂C₆H₅ |
| 99 | -NHCH₂-(pyridyl) |
| 100 | -NHCH₂CH=CH₂ |
| 101 | -NHCH₂C(CH₃)=CH₂ |
| 102 | -NHCH₂C(Cl)=CH₂ |
| 103 | -NHCH₂C≡CH |
| 104 | -NHCH(CH₃)₂C≡CH |
| 105 | -N(CH₃)CH₂C≡CH |
| 106 | -NH-(cyclopropyl) |
| 107 | -NH-(cyclopentyl) |

TABLE II-continued

| Ex. No. | Y |
|---|---|
| 108 | —NH—cyclohexyl |
| 109 | —NH—cyclopentenyl |
| 110 | —NH—cyclohexenyl |
| 111 | —NH—(pyrrolidin-3-yl with NH) |
| 112 | —N(aziridinyl) |
| 113 | —N(pyrrolidinyl) |
| 114 | —N(piperidinyl) |
| 115 | —N(2,5-dihydropyrrolyl) |
| 116 | —N(tetrahydropyridinyl) |
| 117 | —N(piperazinyl)NH |
| 118 | —N(4-methylpiperazinyl) N—CH₃ |
| 119 | —N(morpholinyl) O |
| 120 | —N(thiomorpholinyl) S |
| 121 | —N(pyrrolidin-3-yl)—NH₂ |
| 122 | —N(pyrrolidin-3-yl)—CH₂NH₂ |
| 123 | —N(pyrrolidin-3-yl)—CH₂N(CH₃)₂ |
| 124 | —N(3-hydroxypyrrolidinyl) OH |
| 125 | —N(3,4-dihydroxypyrrolidinyl) OH, OH |
| 126 | —NHC₆H₆ |
| 127 | —NH—C₆H₄—F (4-F) |
| 128 | —NH—cyclohexyl(2,4-diF) |
| 129 | —NH—C₆H₄—OH (4-OH) |
| 130 | —NH—cyclohexyl—NH₂ |
| 131 | —NH—C₆H₄—N(CH₃)₂ |
| 132 | —NH—pyridyl |
| 133 | —NH—thiazol-2-yl |
| 134 | —N(imidazolyl) |

TABLE II-continued

| Ex. No. | Y |
|---|---|
| 135 | —NH—[N-methylimidazole] |
| 136 | —NH—[furan] |
| 137 | —NH—[thiophene] |
| 138 | —NH(CH₂)₂S—S—(CH₂)₂NH₂ |
| 139 | —NH(CH₂)₂S—S—(CH₂)₂NHC(=O)CH₃ |
| 140 | —NH(CH₂)₂S—S—C₆H₅ |
| 141 | —NH(CH₂)₂S—S—(CH₂)₂OH |
| 142 | —NH(CH₂)₂S—S—CH₂C₆H₅ |
| 143 | —NH(CH₂)₂S—S—CH₂—[N-methylimidazole] |
| 144 | —NH(CH₂)₂S—S—[pyridine] |
| 145 | —NH(CH₂)₂S—S—[C₆H₄—NH₂] |
| 146 | —NH(CH₂)₂S—S(CH₂)₂NHC(=O)(CH₂)₂CH(NH₂)CO₂H |
| 147 | —NH(CH₂)₂S—S—[C₆H₄—F] |
| 148 | —NH(CH₂)₂S—S—[C₆H₄—NO₂] |

EXAMPLE 149

In vitro antitumor screening results

As shown in Table III the compounds of the present invention exert an in vitro antitumor effect. The following cells lines were employed: human lung (A549); resistant human lung with low topo II activity (A549-VP); murine melanoma (B16); human colon tumor (HCT116); human colon tumor with elevated p170 levels (HCTVM); human colon tumor with low topo II activity (HCTVP); and another human colon carcinoma cell line (Moser). In the Table, the designation "NT" indicates the compound was not tested against the specified cell line. The cell lines were maintained in continuous culture at 37°, 5% $CO_2$ and high humidity. Cells were harvested in log phase growth and suspended at concentration of 25,000 cells/mL. A 150 mL aliquot was then added to each well (i.e., 3,750 cells per well) of a 96-well flat bottom plate and the cells were allowed to attach over a 24 hour period. After this 24 hour incubation, a 50 μL sample of the specified compound was added to the first (top) well of each column, and the remaining wells of each column serially diluted, 1:4, and allowed to incubate for 72 hours at 37° C., 5% $CO_2$ and high humidity. Following incubation, 50 μL of freshly prepared stain solution was added to each well. After a 3 hour incubation at room temperature, absorbance was read at 450 nm on a microplate reader to determine the compound concentration at which 50% of the cells were killed, such concentration referred to as the "$IC_{50}$".

TABLE III

In Vitro Microdilution Inhibition Concentrations

| Ex. No. | $IC_{50}$ (μg/mL) | | | | | | |
|---|---|---|---|---|---|---|---|
| | A549 | A549VP | B16 | HCT | HCTVM | HCTVP | MOSER |
| 2. | 0.36 | NT | 0.14 | 0.25 | NT | 0.29 | 1.07 |
| 3. | 1.14 | NT | 0.88 | 1.13 | NT | 0.86 | 3.07 |
| 4. | 1.5 | 2.3 | 1.0 | 0.3 | 0.3 | 0.4 | NT |
| 5. | 0.4 | 1.1 | 0.7 | 0.09 | 0.2 | 0.2 | NT |
| 6. | 4.9 | 6.4 | 5.2 | 1.6 | 1.7 | 3.5 | NT |
| 7. | 5.0 | 8.5 | 7 | 1.2 | NT | 1.2 | 5.9 |
| 8. | 24.5 | 26.5 | 18 | 14.5 | NT | NT | 18.3 |
| 9. | 4.42 | NT | 0.78 | 0.71 | NT | 2.38 | 4.4 |
| 11. | <0.03 | 0.03 | 0.03 | 0.03 | 0.03 | 0.03 | NT |
| 12. | <0.03 | 0.05 | 0.03 | 0.03 | 0.05 | 0.03 | 0.03 |
| 13. | <0.03 | 0.05 | 0.03 | 0.03 | 0.03 | 0.04 | NT |
| 14. | <0.03 | 0.03 | 0.03 | 0.03 | 0.03 | 0.03 | NT |
| 15. | <0.03 | 0.05 | 0.03 | 0.03 | 0.03 | 0.05 | NT |
| 16. | <0.03 | 0.04 | 0.03 | 0.05 | 0.06 | 0.04 | NT |
| 17. | NT | NT | 15 | 1.47 | NT | NT | NT |
| 18. | 0.08 | 0.06 | 0.08 | 0.09 | 0.11 | 0.07 | NT |
| 19. | NT | NT | 27 | 322 | NT | NT | NT |
| 20. | >16 | >16 | >16 | >16 | >16 | >16 | >16 |
| 21. | NT | NT | 18.7 | 6.79 | NT | NT | NT |
| 23. | 0.14 | 0.1 | 0.39 | 0.28 | 0.22 | 0.1 | NT |
| 24. | 0.5 | 1.4 | 0.4 | 0.2 | 0.7 | 1.1 | NT |
| 25. | 0.14 | 0.16 | 0.14 | 0.27 | 0.22 | 0.13 | NT |
| 26. | NT | NT | 9.30 | 1.23 | NT | NT | NT |

TABLE III-continued

| | In Vitro Microdilution Inhibition Concentrations | | | | | | |
|---|---|---|---|---|---|---|---|
| | $IC_{50}$ (μg/mL) | | | | | | |
| Ex. No. | A549 | A549VP | B16 | HCT | HCTVM | HCTVP | MOSER |
| 27. | NT | NT | 0.24 | NT | NT | 0.22 | NT |
| 28. | NT | NT | >500 | 71 | NT | NT | NT |
| 29. | 1.2 | 1.6 | 0.8 | 0.9 | 1.0 | 1.0 | NT |
| 30. | 7.0 | >16 | 1.8 | 1.2 | 3.0 | 2.2 | NT |
| 31. | >16 | >16 | >16 | >16 | >16 | >16 | NT |
| 32. | >16 | >16 | >16 | >16 | >16 | >16 | NT |
| 33. | NT | NT | 107 | 5.08 | NT | NT | NT |
| 34. | NT | NT | 110 | 78 | NT | NT | NT |
| 35. | NT | NT | 24 | NT | NT | 22 | NT |
| 36. | NT | NT | 458 | >500 | NT | NT | NT |

EXAMPLE 150

In vivo antitumor test results

The in vivo potency of the compounds of the present invention is exemplified by the data set forth in Table IV. $CDF_1$ mice of both sexes weighing between 16 and 25 gm. were used, with a 2 gm. weight range and same sex and source used per experiment. $BDF_1$ mice also were used with the same weight, sex and source parameters. Control and test animals were injected interperitoneally with suspension of $1 \times 10^6$ p388 murine leukemia cells (0.5 mL dose) on day 0. Groups of 4–6 mice were used for each dosage amount they were treated with 5 doses on day one. A group of ten saline treated control mice was included in each set of experiments. A 30 day protocol was employed with mean survival time in days being determined for each group of mice with the number of survivors at the end of the 30 day period being noted. The mice were weighed before treatment and again on day five. The values listed for average weight change (AWC) is the average weight change per mouse at the specified dose. The change in weight was taken as a measure of drug toxicity. A loss in weight of up to 2 grams is not considered excessive. The results were determined in terms of % T/C which is the ratio of the mean survival time of the treated group to the mean survival time of the saline treated group times 100.

TABLE IV

| | In Vivo Activity of Compounds Against | | | |
|---|---|---|---|---|
| | p388 Murine Leukemia In An Acute Mouse Model | | | |
| Ex. No. | HOST | DOSE (MG/KG) | % T/C DOSE | AWC |
| 2. | CDF1 (mixed sex) | 45 | Toxic | — |
| | | 15 | 110 | −1.3 |
| | | 5 | 105 | −0.1 |
| 7. | CDF1 (female only) | 45 | Toxic | — |
| | | 15 | 150 | −3.8 |
| | | 5 | 150 | −2.8 |
| 8. | BDF1 (female only) | 45 | 145 | −2.8 |
| | | 15 | 135 | −1.5 |
| | | 5 | 125 | 1.0 |
| 15. | CDF1 (mixed sex) | 45 | Toxic | — |
| | | 15 | 115 | −0.2 |
| | | 5 | 100 | −0.1 |
| 16. | CDF1 (female only) | 30 | 130 | −2.6 |
| | | 10 | 95 | −1.1 |
| | | 3.3 | 95 | −0.1 |
| 22. | CDF1 (female only) | 30 | 135 | −0.2 |
| | | 10 | 105 | 1.0 |
| | | 3.3 | 95 | 1.5 |
| 24. | CDF1 (mixed sex) | 45 | 120 | −0.9 |
| | | 15 | 110 | −0.3 |
| | | 5 | 110 | −0.3 |
| 25. | CDF1 (female only) | 36 | 120 | −1.6 |
| | | 12 | 105 | −0.7 |
| | | 4 | 125 | 0.9 |
| 23. | CDF1 (female only) | 36 | 100 | 0.7 |
| | | 12 | 95 | 1.7 |
| | | 4 | 100 | 1.8 |

What is claimed is:

1. A compound having the Formula (I):

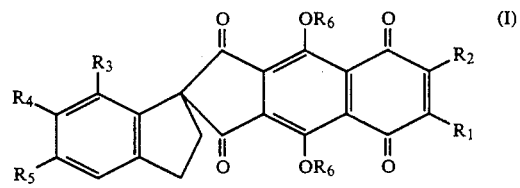

wherein:

$R_1$ and $R_2$ are each independently selected from the group consisting of:

hydrogen, halo, hydroxy, arylthio having from 6 to 10 carbon atoms, alkylthio having from 1 to 8 carbon atoms, alkylthio having from 1 to 8 carbon atoms independently substituted at available positions by one or more hydroxy, halo, nitro, cyano, alkoxy having from 1 to 8 carbon atoms, amino, alkylamino having from 1 to 8 carbon atoms, $C_{1-8}$-alkoxycarbonylamino, guanidino, ureido, $C_{1-8}$-alkylureylene, alkanoylamino, $C_{1-8}$-alkoxycaboxyl, alkenyl having 2 to 6 carbon atoms, alkynyl having 2 to 6 carbon atoms, cycloalkyl having 3 to 7 ring members, cycloalkenyl having 5 to 7 ring members and a group of the formula —S—S—R' wherein R' is selected from the group consisting of alkyl having from 1 to 8 carbon atoms, cycloalkyl having from 3 to 7 ring members, alkanoylamino, aryl having from 6 to 10 carbon atoms, and aryl having from 6 to 10 carbon atoms substituted by alkyl having from 1 to 8 carbon atoms, and a group of the Formula $-N(R_7)R_8$ wherein $R_7$ and $R_8$ are each independently selected from the group consisting of hydrogen, hydroxy, alkyl having from 1 to 8 carbon atoms, alkenyl having from 2 to 6 carbon atoms, alkynyl having 2 to 6 carbon atoms, alkoxy having from 1 to 8 carbon atoms, $C_{1-8}$-alkoxycarbonyl, alkanoyl, cycloalkyl having 3 to 7 ring members, aryl having from 6 to 10 carbon atoms, aryl having 6 to 10 carbon atoms substituted by alkyl having from 1 to 8 carbon atoms, $C_{6-10}$-arylcarbonyl, amidino, and dialkylaminocarbonyl having 3 to 12 carbon atoms;

$R_3$ is selected from the group consisting of hydrogen, hydroxy, alkyl having from 1 to 8 carbon atoms, and alkoxy having from 1 to 8 carbon atoms;

$R_4$ and $R_5$ together form a ring selected from the following Formulas (IA) and (IB):

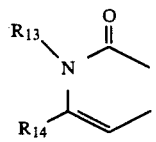
(IA)

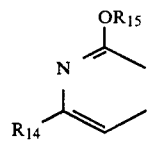
(IB)

wherein $R_{13}$ is selected from the group consisting of hydrogen and alkyl having from 1 to 8 carbon atoms; $R_{14}$ is selected from the group consisting of alkyl having from 1 to 8 carbon atoms, alkenyl having 2 to 8 carbon atoms, alkanoyl, and alkyl having from 1 to 8 carbon atoms; $R_{15}$ is selected from the group consisting of hydrogen, alkyl having from 1 to 8 carbon atoms, and alkanoyl;

$R_6$ is selected for the group consisting of hydrogen, alkanoyl, $C_{6-10}$-aryl carbonyl, and a pharmaceutically acceptable cation; and pharmaceutically acceptable salts thereof.

2. A compound of claim 1 where $R_{14}$ is alkenyl having 2 to 10 carbon atoms.

3. A compound of claim 3 where $R_{14}$ is pentadienyl.

4. A compound of claim 1 where at least one of $R_1$ and $R_2$ is hydrogen.

5. The compound of claim 1 which is 6',7'-Dihydro-1-methoxy-9'-(methoxymethoxy)-3'-(n-pentyl)-spiro[2H-benz[f]indene-2,8'[8H]cyclopent[g]isoquinoline]-1,3,5,8-tetrone.

6. The compound of claim 1 which is 2',6',7'-Trihydro-4,9,9'-trihydroxy-3'-(n-pentyl)-spiro[2H-benz[f]-indene-2,8'-8H]cyclopent[g]isoquinoline]-1,1',3,5,8-pentone.

7. The compound of claim 1 which is 6',7',-Dihydro-1-methoxy-9'-(methoxymethoxy)-3'-formyl-spiro[2H-benz[f]indene-2,8'-[8H]cyclopent[g]isoquinoline]-1,3,5,8-tetrone.

8. A pharmaceutical composition comprising a pharmaceutically acceptable carrier and an antitumor effective amount of a compound of claim 1.

9. A pharmaceutical composition comprising a pharmaceutically acceptable carrier and an antitumor effective amount of a compound of claim 2.

10. A method of inhibiting growth of a mammalian tumor which comprises administering to a mammal bearing a tumor an antitumor effective amount of a compound of claim 1.

11. A method of inhibiting growth of a mammalian tumor which comprises administering to a mammal bearing a tumor an antitumor effective amount of a compound of claim 2.

* * * * *